United States Patent [19]

Kaiser

[11] Patent Number: 4,677,242
[45] Date of Patent: * Jun. 30, 1987

[54] PRODUCTION OF LIGHT OLEFINS

[75] Inventor: Steven W. Kaiser, South Charleston, W. Va.

[73] Assignee: Union Carbide Corporation, Danbury, Conn.

[*] Notice: The portion of the term of this patent subsequent to Feb. 12, 2002 has been disclaimed.

[21] Appl. No.: 700,311

[22] Filed: Feb. 11, 1985

Related U.S. Application Data

[63] Continuation-in-part of Ser. No. 426,213, Oct. 4, 1982, Pat. No. 4,499,327.

[51] Int. Cl.⁴ .............................................. C07C 1/00
[52] U.S. Cl. ................................. 585/638; 585/639; 585/640
[58] Field of Search ............... 585/638, 639, 640, 469, 585/733, 357, 603

[56] References Cited

U.S. PATENT DOCUMENTS

| | | | |
|---|---|---|---|
| 4,373,109 | 2/1983 | Olah | 585/638 |
| 4,440,871 | 4/1984 | Lok et al. | 502/214 |
| 4,499,327 | 2/1985 | Kaiser | . |
| 4,524,234 | 6/1985 | Kaiser | 585/638 |

FOREIGN PATENT DOCUMENTS 911410 10/1972 Canada .
WO82100018 6/1982 PCT Int'l Appl. .

*Primary Examiner*—John Doll
*Assistant Examiner*—Chung K. Pak
*Attorney, Agent, or Firm*—Vincent J. Vasta, Jr.

[57] ABSTRACT

The process for the production of light olefins from a feedstock comprising at least an aliphatic hetero compound comprising contacting said feedstock in the presence of an aromatic diluent with a silicoaluminophosphate molecular sieve at effective process conditions to produce light olefins.

38 Claims, 2 Drawing Figures

PRODUCTION OF LIGHT OLEFINS

REFERENCE TO RELATED APPLICATION

This application is a continuation-in-part of copending U.S. Ser. No. 426,213, filed Oct. 4, 1982 now U.S. Pat. No. 4,499,327, issued Feb. 12, 1985.

FIELD OF THE INVENTION

The present invention relates to a new catalytic process for the production of light olefins, i.e., olefins having not more than four carbon atoms, from a feedstock comprising aliphatic hetero compounds or mixtures thereof in the presence of a silicoaluminophosphate molecular sieve catalyst and diluent correlated to the silicoaluminophosphate molecular sieve such that the average kinetic dimater of the diluent is greater than the median pore size of the silicoaluminophosphate molecular sieve.

BACKGROUND OF THE INVENTION

As a result of the limited availability and high cost of petroleum sources the cost of producing chemicals from such petroleum sources has been steadily increasing. Further, many in the chemical industry, as well as elsewhere, have raised the dire prediction of significant oil shortages in the not too distant future. As a result, the search for an alternative, low cost and more readily available raw material for chemical synthesis has been intense with the ultimate goal being the derivation of valuable chemical products from non-petroleum sources.

Such readily available sources are methanol, ethanol and their derivatives which may be manufactured from non-petroleum sources such as by fermentation or from synthesis gas, i.e. a mixture of oxides of carbon and hydrogen. Synthesis gas may be derived by the combustion of any carbonaceous material including coal, or any organic material, such as hydrocarbons, carbohydrates and the like. Thus, the use of methanol and its derivatives to form chemical products is particularly desirable in providing such a non-petroleum based route. The manufacture of methanol from synthesis gas by a heterogeneous catalytic reaction is presently an efficient commercial process.

Although methanol and its derivatives have for some time being considered as desirable starting materials for the manufacture of chemicals (which it is, e.g., in the manufacture of formaldehyde), the use of such as a replacement for petroleum or natural gas in commercial chemical syntheses has not been vast. if processes can be developed for the use of methanol and its derivatives for the commercial manufacture in large volume of chemical products or intermediates then the present dependence on petroleum sources as the basic raw material for chemical synthesis may be substantially lessened.

One proposed way to use methanol and its derivatives to manufacture chemical products is by catalytically converting them with crystalline aluminosilicate zeolites. Representative of the various contemplated processes using such crystalline aluminosilicate, zeolites, and as more completely discussed hereinafter, are those processes disclosed in U.S. Pat. Nos.: 3,894,107; 4,046,825; 4,062,905; 4,079,095; 4,079,096; 3,911,041; and 4,049,573. What appears to be evident from the above patents, as well as other patents, is that the process is tied to the particular catalyst employed yielding differences in: product ratios (as well as by-product formation); catalyst life; conversion to product; selectivity to product; catalyst attrition; and the effects from additives to the catalytic process. The significance of these differences is readily apparent by reviewing the divergent results of the published art wherein various catalysts have been employed for the conversion of methanol to light olefin products. Representative of this art are: European Application No. 6,501 (catalyst is HZSM-5); European Application No. 2,492 (catalyst is Mn exchanged 13X zeolite); German Offen. No. 2,909,928 (catalyst is Fe exchanged Silicalite); Angew. Chem. Int. Ed., 19, 2 (1980), 126-7 (catalyst is Mn exchanged Chabazite and erionite); South African No. 78/2527 (catalyst is CaH-Fu-1 zeolite); and European Application No. 11,900 (catalyst is boron modified silica).

For example, German Offen. No. 2,909,928 discloses a 95-100 percent conversion with 5.2 weight percent of the product as ethylene, whereas the publication Angew. Chem. Int. Ed., 19, 2 (1980), 126-7 discloses a conversion of about 82 percent with 35.7 weight percent of the product as ethylene.

A brief discussion of selected patents and publications will further serve to point out differences involved in the conversion of methanol and derivatives thereof to light olefin products.

U.S. Pat. No. 4,062,905 discloses a process for the conversion of methanol, dimethyl ether or mixtures thereof to hydrocarbon products rich in ethylene and propylene using a catalyst comprising a crystalline aluminosilicate zeolite characterized by pores, the major dimension of which, are less than 6 Angstroms, the pores being further characterized by pore windows of about a size as would be provided by 8-membered rings of oxygen atoms. The process is alleged to have the capability under certain conditions of producing less than 20 weight percent methane by weight of the hydrocarbon product. The claimed correlation in the patent between pore size, process conditions and the level of methane production is admittedly specifically limited to the crystalline aluminosilicate zeolites, see the quote below.

The passage beginning at column 3, line 5 (also see Example 17) of U.S. Pat. No. 4,062,905 demonstrates this view:

"In addition to having the hereinabove described pore size characteristics, the crystalline aluminosilicate zeolite utilized as catalyst in the present process should have the capability of producing a hydrocarbon product containing less than 20 percent and preferably not more than 10 percent by weight of methane. Thus, the calcium form of zeolite A, having pores of approximately 5 Angstroms and commonly referred to as zeolite 5 A, while satisfying the pore size requirements for zeolites useful as catalysts in the process described herein, is nevertheless, not a particularly feasible catalyst since under the conversion conditions utilized in such process, this zeolite produces considerable amounts of methane, i.e. far in excess of the specified maximum of 20 weight percent characterizing the crystalline aluminosilicate zeolites which have been found to be effective in selectively converting methanol and/or dimethyl ether to ethylene and propylene."

Even when a crystalline aluminosilicate zeolite having the desired physical and chemical properties is employed it may not be useful as a catalyst according to the patent's process. Thus, this patent discloses that the chemical composition of an aluminosilicate which has a desirable pore size may or may not be determinative as to whether it will produce methane at a given rate such that less than 20 percent by weight methane is produced.

The specificity of the catalysts in this field is demonstrated by U.S. Pat. Nos. 4,079,096 and 4,079,095 which disclose processes for the conversion of methanol, dimethyl ether of mixtures thereof to hydrocarbon products, such as ethylene and propylene, by contacting them with a catalyst comprising, respectively, a crystalline aluminosilicate zeolite of the erionite-offretite family and, the particular erionite-offretite of the crystalline aluminosilicate zeolite ZSM-34. The processes are limited to the use of crystalline aluminosilicates having substantially the same diffraction pattern as the erionite-offretite family.

U.S. Pat. No. 3,911,041 describes the conversion of methanol or dimethyl ether by contacting them with a crystalline aluminosilicate zeolite having a silica to alumina ratio of at least about 12, a constraint index of about 1 to 12, and containing phosphorous deposited on the crystal structure thereof in an amount of at least about 0.78 percent by weight. The phosphorous is disclosed as not in the framework of the crystalline aluminosilicate, as can be determined from the preparation procedure beginning at column 7, line 56 of the patent. The procedure set forth in the patent details that the crystalline aluminosilicate zeolite is formed prior to the addition of the phosphorus-containing compound, after which the phosphorous-containing compound is "reacted" with the surface sites of the zeolite to provide a surface treated material. Further, X-ray diffraction analyses of the zeolite before and after treatment with a phosphorus- containing compound showed substantially identical interplanar spacings (see Column 8, lines 54 to 64) indicating that no phosphorus was present in the framework. The surface treatment of the crystalline aluminosilicates is predicated on the patentees' belief that the number and strength of the aluminosilicate acid sites is related to the activity.

U.S. Pat. No. 4,049,573 describes a crystalline aluminosilicate zeolite having a silica to alumina ratio of at least 12 and a constraint index within the approximate range of 1 to 12, and having deposited thereon (as one of several possibilities) between about 0.25 and about 10 percent by weight of phosphorus oxide in combination with between about 0.25 and about 5 percent by weight of boron oxide and between about 2 and about 15 percent by weight of magnesium oxide. As was the case in the above-discussed U.S. Pat. No. 3,911,041, the phosphorous oxide, boron oxide and magnesium oxide are not incorporated into the zeolite framework but, instead, are added to the zeolite after the framework of the aluminosilicate zeolite has been formed, i.e. are provided as a post treatment of the aluminosilicate zeolite, apparently for the same reason.

As is evident from the above, the interest in selective catalysts for the manufacture of light olefins from methanol has been achieved from a special aluminosilicate structure or by achieving modifications of aluminosilicates by deposition with special additives. As above-noted, one of these was to deposit a phosphorous-containing compound (termed "doping" herein) in combination with a number of other compounds on an aluminosilicate zeolite.

U.S. Pat. Nos. 3,911,041 and 4,049,573, reports the sorption of phosphate ions onto amorphous metal oxides and combinations of metal oxides. Such sorptions of phosphate ions has been intensively studied in such areas as in the chemistry of soil, although such studies have not heretofore reported a crystalline microporous phosphate-containing material. For example, see: S. S. S. Rajan and K. W. Perrott, J. Soil Sci., 26, 257 (1975); J. A. Veith and G. Sposito, Soil. Sci., Soc. Am. J., 41, 870 (1977); E. A. Ferreiro and S. G. DeBussetto, Agrochimica, 24,184 (1980).

It has been reported (D. McConnell, Ameri. Min., 37, 609 (1952)) that certain natural aluminosilicate zeolites may have $PO_2^+$ substitution into the tetrahedral framework with such a substitution being reported in viseite which is considered to be isostructural with analcime. D. McConnell reported an elemental composition of:

$$5CaO:5Al_2O_3:3SiO_2:3P_2O_5 \cdot nH_2O.$$

This report should be viewed cautiously, if not with skepticism, in view of the considerable question of agreement on the X-ray powder diffraction patterns of such a substituted viseite and analcime owing to the highly defective structure (with dangling —OH groups wherever tetrahedral cation vacancies occur) resorted to in order to substantiate such structures as being isostructural.

R. M. Barrer and D. J. Marshall (J. Chem. Soc., 1965, 6616 and 6621) reported the attempted substitution of phosphorus in aluminosilicates during hydrothermal crystallizations in the system, in respect to the following:

$$Al_2O_3-SiO_2-P_2O_5-base-H_2O$$

Although phosphate was observed to co-precipitate with the aluminosilicates in this system there was no evidence that an aluminosilicophosphate framework had formed.

R. M. Barrer and M. Liquornick (J. Chem. Soc., Dalton Trans., 2126 (1974)) reported that by use of metakaolinite and phosphoric acid, and in some instances by further addition of silica, that zeolites were formed having an extremely low content of phosphorous with a maximum of 0.0117 atoms of phosphorus present per atom of aluminium. The authors' explanation for this very low phosphorous content is that phosphate anions were trapped in cavities within the zeolite framework rather than actually being in the framework.

U.S. Pat. No. 3,443,892 discloses a process for making Zeolite X by mixing aluminum phosphate with hot sodium silicate to give an as-synthesized product having the general formula:

$$(0.5-1.1)Na_2O_3:Al_2O_3:(0-0.2)P_2O_5:(2.3-3.3)SiO_2:(0-7.2)H_2O$$

No chemical data are disclosed by the patentee for determining the framework structure, and the patent requires that the ratio of $SiO_2$ to $Na_2O$ in the reaction mixture must be less than 1.

The synthesis of aluminosilicophosphate zeolite analogues having phosphorus incorporated into the tetrahedral sites of the zeolite-type framework during hydrothermal synthesis employing substantial amounts of alkali metal cations has been reported by E. M. Flanigen and R. W. Grose at Advances in Chem., Series No. 101 pages 76–101 (1971). (Also see: Canadian Patent No. 911,410, issued Oct. 3, 1972 to Robert W. Grose and Edith M. Flanigen.) In this report the authors reported compositions with the following types of zeolite-type frameworks: analcime, chabazite, phillipsite-harmotome, Type A zeolite, Type L zeolite, and Type B (P) zeolite. These compositions were reported to contain between 5 and 25 percent by weight $P_2O_5$ incorporated into the zeolite-type frameworks. The substitution of phosphorus for silicon did not appear to impart beneficial properties to the compositions not possessed by analogous aluminosilicate compositions, although differences were reported in some of the compositions, e.g. reduced adsorption capacity and reduced thermal stability on thermal activation. Many of the physical and chemical properties of the phosphorus-substituted analogues were inferior to those of the unsubstituted species.

IN THE DRAWINGS

DISCLOSURE OF THE INVENTION

Figure 1:
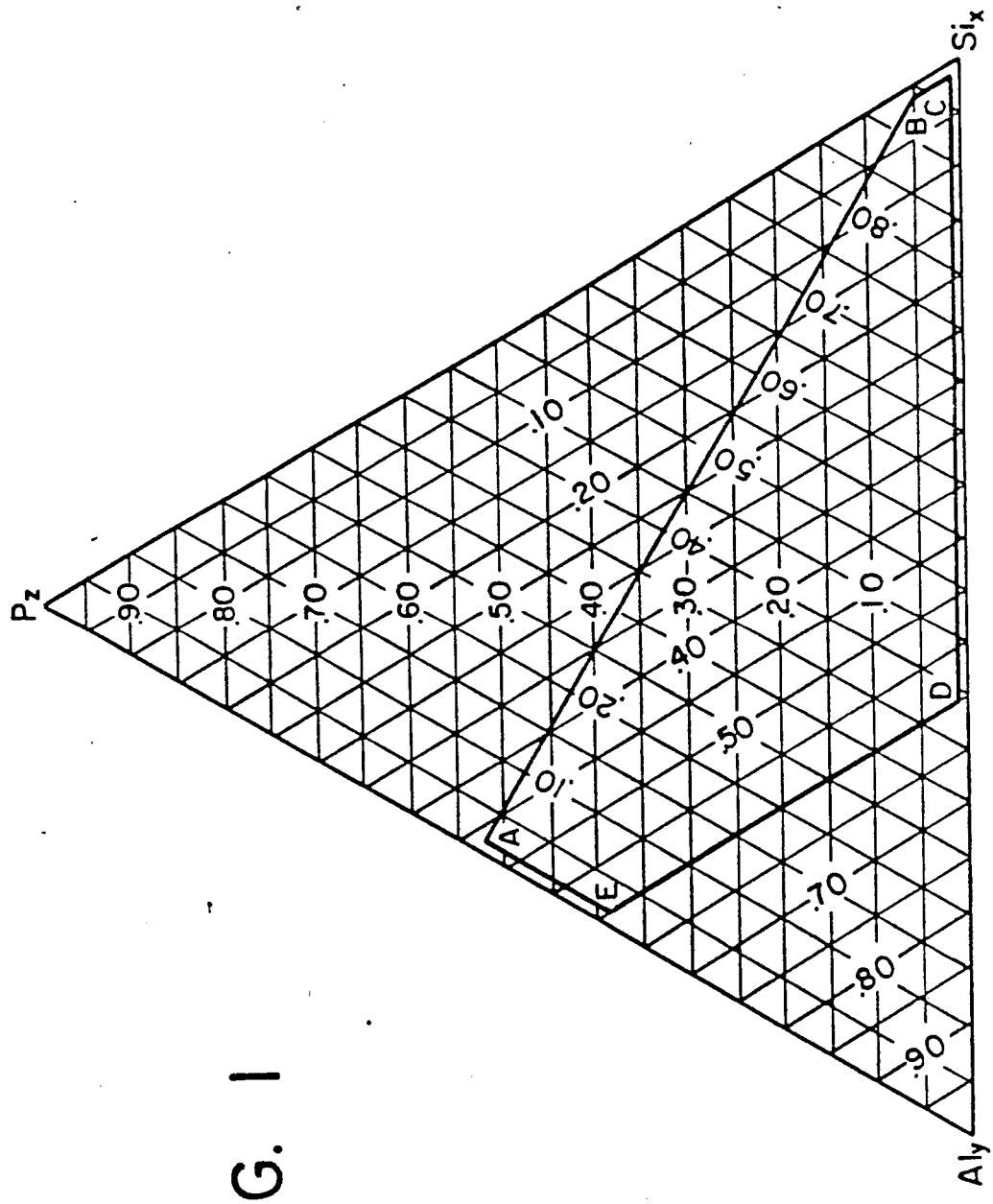
FIG. 1 is a ternary diagram showing the compositional parameters of the silicoaluminophosphates useful in the process of this invention in terms of mole fractions of silicon, aluminum and phosphorus.

This invention comprises a process for the catalytic conversion of a feedstock comprising one or more aliphatic hetero compounds comprising alcohols, halides, mercaptans, sulfides, amines, ethers and carbonyl compounds or mixtures thereof to a hydrocarbon product containing light olefinic products, i.e., $C_2$, $C_3$ and/or $C_4$ olefins. The feedstock is contacted with a silicoaluminophosphate molecular sieve in the presence of a diluent at effective process conditions to produce light olefins. The diluent is correlated to the selected silicoaluminophosphate such that the average kinetic diameter of the diluent is greater than the median pore size of the silicoaluminophosphate molecular sieve. Silicoaluminophosphate molecular sieves which produce light olefins are generally employable in the instant process. The preferred silicoaluminophosphates are those described in U.S. Pat. No. 4,440,871. Silicoaluminophosphate molecular sieves employable in the instant process are more fully described hereinafter.

It has been found that silicoaluminophosphate molecular sieves (denominated "SAPOs") in the presence of a diluent having an average kinetic diameter larger than the pores of the SAPOs are extremely efficient catalysts for the conversion of a feedstock comprising aliphatic hetero compounds, preferably methanol, ethanol, dimethyl ether, diethyl ether or mixtures thereof, to light olefins and that the two carbon, three carbon, and four carbon ($C_2$–$C_4$) light olefin product content of the hydrocarbon reaction products generally comprises a major portion of the hydrocarbon products while methane and aromatics (other than the diluent) typically comprise a minor portion thereof.

DESCRIPTION OF THE INVENTION

The instant process relates to making light olefins containing 2 to 4 carbon atoms wherein said process comprises contacting a feedstock with a silicoaluminophosphate molecular sieve comprising a molecular framework of $[AlO_2]$, $[PO_2]$ and $[SiO_2]$ tetrahedral units, at effective process conditions in the presence of a diluent to produce such light olefin products. The selection of the diluent is correlated to the silicoaluminophosphate such that the average kinetic diameter of the diluent is greater than the median pore size of the silicoaluminophosphate molecular sieve. The preferred diluents are aromatic diluents. It should be noted that the $[AlO_2]$ tetrahedral unit has a net negative charge and the $[PO_2]$ tetrahedral unit has a net positive charge, although such are not designated herein as such.

The term "light olefins" will be used hereinafter to refer to olefins having two to four carbons atoms, inclusive. Although other hydrocarbon products are formed, the products of particular interest herein are the light olefins and they are preferably produced as the major hydrocarbon products i.e., over 50 mole percent of the hydrocarbon product is light olefins. The effect of correlating the kinetic diameter of the diluent to the silicoaluminophosphate molecular sieves in the catalytic formation of light olefins, preferably as the major portion of the hydrocarbon product, has not heretofore been reported or suggested.

It is disclosed in copending U.S. Ser. No. 426,213 now U.S. Pat. No. 4,499,323, issued Feb. 12, 1985 that by use of silicoaluminophosphate molecular sieves as the catalyst(s) for the conversion of such a feedstock that, in general, higher feedstock conversions and selectivities (sometimes referred to as the "Molar Efficiency") to light olefin products may be obtained as compared to that obtained by use of the prior art aluminosilicate zeolites as catalysts.

It has been discovered that by correlating the silicoaluminophosphate molecular sieves and diluent, e.g., an aromatic diluent, selectivity to $C_2$ to $C_4$ olefin products (i.e., ethylene, propylene, and butenes) of at least about 25 molar percent, based on the total hydrocarbon products formed, may be obtained, preferably in excess of 50 mole percent. Further, the selectivity for the conversion of aliphatic hetero compounds to such olefin products may be in excess of 75 mole percent when specific silicoaluminophosphate molecular sieves are employed. Further, high molar conversions, i.e., perferably at least about 70 percent and most preferably at least about 90 percent, based on the moles of feedstock to products, may be obtained while forming a minimum molar amount of methane (less than about ten (10) molar percent and preferably less than about five (5) molar percent) and while forming only minor amounts of saturated hydrocarbons and $C_5$ and higher hydrocarbons (typically less than about 10 molar percent). In addition, it has been observed that the formation, if any, of aromatic hydrocarbons (exclusive of the aromatic diluent) is below that which is detectable by standard vapor phase chromatographic techniques. An additional bonus is that certain silicoaluminophosphate molecular sieves as employed in the instant process are believed to have increased catalyst life with respect to the conversion of the instant feedstock to light olefin products as compared with the crystalline aluminosilicates ( e.g. the ZSM-type). (For example, see example 2 of U.S. Pat. No. 4,079,095).

The instant process provides improved ethylene to propylene molar ratios by carrying out the process in the presence of a diluent correlated to the selected SAPO.

The instant process employs a feedstock comprising "aliphatic hetero compounds". The term "aliphatic hetero compounds" is employed herein to include alcohols, halides, mercaptans, sulfides, amines, ethers and carbonyl compound (aldehydes, ketones, carboxylic acids, esters and the like). The aliphatic moiety preferably contains from 1 to about 10 carbon atoms and more preferably contains from 1 to about 4 carbon atoms. Suitable reactants include lower straight and branched chain alkanols, their unsaturated counterparts, and the nitrogen halogen and sulfur analogue of such. Representative of suitable aliphatic hetero compounds include: methanol; methyl chloride, methyl mercaptan; methyl sulfide; methyl amines; dimethyl ether; ethanol; ethyl mercaptan; ethyl chloride; diethyl ether; methylethyl ether; formaldehyde; dimethyl ketone; acetic acid; n-alkyl amines; n-alkyl halides and n-alkyl sulfides having n-alkyl group having 3 to 10 carbon atoms; and mixtures thereof.

The instant process is preferably carried out in the vapor phase such that the feedstock is contacted in a vapor phase in a reaction zone with a silicoaluminophosphate molecular sieve at effective process conditions such as to produce light olefins, i.e., an effective temperature, pressure, WHSV (Weight Hourly Space Velocity) and with an effective amount of diluent to produce light olefins. Alternatively, the process may be carried out in a liquid phase. When the process is carried out in the liquid phase the process necessarily involves the separation of products formed in a liquid reaction media and can result in different conversions and selectivities of feedstock to product with respect to the relative ratios of the light olefin products as compared to that formed by the vapor phase process.

The temperature which may be employed in the process may vary over a wide range depending, at least in part, on the selected silicoaluminophosphate catalyst. In general, the process can be conducted at an effective temperature between about 200° C. and about 700° C., preferably between about 250° C. and about 600° C., and most preferably between about 300° C. and about 500° C. Temperatures outside the stated range are not excluded from the scope of this invention, although such do not fall within certain desirable embodiments of the invention. At the lower end of the temperature range and, thus, generally at the lower rate of reaction, the formation of the desired light olefin products may become markedly slow. At the upper end of the temperature range and beyond, the process may not form an optimum amount of light olefin products. Notwithstanding these factors, the reaction will still occur and the feedstock, at least in part, can be converted to the desired light olefin products at temperatures outside the range between about 200° C. and about 700° C.

The process is effectively carried out over a wide range of pressures including autogenous pressures. At pressures between about 0.001 atmospheres and about 1000 atmospheres, the formation of light olein products will be effected although the optimum amount of product will not necessarily form at all pressures. The preferred pressure is between about 0.01 atmospheres and about 100 atmospheres. The pressures referred to herein for the process are exclusive of the diluent, and refer to the partial pressure of the feedstock as it relates to the aliphatic hetero compounds and/or mixtures thereof. Pressures outside the stated range are not excluded from the scope of this invention, although such do not fall within certain desirable embodiments of the invention. At the lower and upper end of the pressure range, and beyond, the selectivities, conversions and/or rates to light olefin products may not occur at the optimum, although light olefin products can be formed.

The process is effected for a period of time sufficient to produce the desired light olefin products. In general, the residence time employed to produce the desired product can vary from seconds to a number of hours. It will be readily appreciated by one skilled in the art that the residence time will be determined to a significant extent by the reaction temperature, the silicoaluminophosphate molecular sieve selected, the WHSV, the phase (liquid or vapor) selected, and, perhaps, selected process design characteristics.

The process is effectively carried out over a wide range of WHSV for the feedstock and is generally between about 0.01 hr$^{-1}$ and about 100 hr$^{-1}$ and preferably between about 0.1 hr$^{-1}$ and about 40 hr$^{-1}$. Values above 100 hr$^{-1}$ may be employed and are intended to be covered by the instant process, although such are not preferred.

The instant process is most preferably carried out under process conditions comprising a temperature between about 300° C. and about 500° C., a pressure between about 0.1 atmosphere (one atmosphere equals 14.7 psia) to about 100 atmospheres, utilizing a WHSV expressed in hr$^{-1}$ for each component of the feedstock having a value between about 0.1 and about 40. The temperature, pressure, and WHSV are each selected such that the effective process conditions, i.e., the effective temperature, pressure, and WHSV, are employed in conjunction, i.e. correlated, with the selected silicoaluminophosphate molecular sieve and selected feedstock such that light olefin products are produced.

The selection of the diluent is such that the diluent is correlated to the selected silicoaluminophosphate such that the average kinetic diameter of the diluent molecules is greater than the average pore size of the silicoaluminophosphate molecular sieve. The selection of the diluent is also related to the relative stability of the diluent under the process conditions. The average pore sizes of the SAPOs are such that the diluent is generally one or more cyclic compounds having 5 or more atoms in the ring, e.g., cycloalkanes, cycloalkenes, pyridine and aromatic compounds. The diluent should be thermally stable under the process conditions. Aromatic compounds employable herein include compounds of the formula:

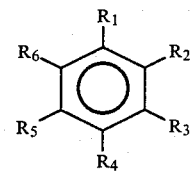

wherein $R_1$, $R_2$, $R_3$, $R_4$, $R_5$, $R_6$ may be alkyl, alkylaryl, araalkyl, aryl and mixtures thereof, containing 1 to 20 carbon atoms and optionally, hetero atoms (S, N, Cl, etc). The diluent may be selected from the group consisting of: cycloalkanes and substituted cycloalkanes (cyclopentane, cyclohexane); pyridine and substituted pyridine; benzene; alkyl benzenes including toluene, o-xylene, m-xylene, p-xylene, hemimellitene, pseudocumene, mesitylene, prehnitene, isodurene, durene, pentamethylbenzene, hexamethylbenzene, ethylbenzene, n-propylbenzene, cumene, n-butylbenzene, isobutylbenzene, sec-butylbenzene, tert-butylbenzene, p-cymene;

biphenyl, diphenylmethane; triphenylmethane; 1,2-diphenylethane; anthracene; naphthalene; and the like.

In addition to the presence of the diluent that is correlated to the selected SAPO as above described, which may be present in an amount between about 1 and about 99 weight percent of the feedstock, and the aliphatic hetero compound(s) in the feedstock, other diluents may be present in the feedstock in place of such diluent in an amount between about 1 and about 80 molar percent, based on the total number of moles of all feed and diluent components fed to the reaction zone (or catalyst). Typical of additional diluents which may be employed in the instant process are helium, argon, nitrogen, carbon monoxide, carbon dioxide, hydrogen, water(steam), paraffins, hydrocarbons (such as methane and the like), mixtures thereof, and the like.

It has been discovered that the addition of a diluent (correlated to the pore sizes of the selected SAPO), e.g., aromatic diluent, to a feedstock comprising aliphatic hetero compounds is beneficial in increasing the molar ratio of ethylene to propylene in the hydrocarbon products. In many processes where ethylene is the desired light olefin this increase in the relative amount of ethylene may be of significant commercial importance.

The instant process may be carried out in a batch, semi-continuous, or continuous fashion. The process can be conducted in a single reaction zone or a number of reaction zones arranged in series or in parallel, or it may be conducted intermittently or continuously in an elongated tubular zone or a number of such zones. When multiple reaction zones are employed, it may be advantageous to employ one or more of such silicoaluminophosphate molecular sieves in series to provide for a desired product mixture. Owing to the nature of the process, it may be desirous to carry out the instant process by use of the silicoaluminophosphates in a dynamic (e.g. fluidized or moving) bed system or any system of a variety of transport beds rather than in a fixed bed system. Such systems would readily provide for any regeneration (if required) of the silicoaluminophosphate molecular sieve catalyst after a given period of time. If regeneration is required, the silicoaluminophosphate molecular sieve catalyst can be continuously introduced as a moving bed to a regeneration zone where it can be regenerated, such as for example by removing carbonaceous materials or by oxidation in an oxygen-containing atmosphere. In the preferred practice of the invention, the catalyst will be subject to a regeneration step by burning off carbonaceous deposits accumulated during reactions.

SILICOALUMINOPHOSPHATES

The selection of the silicoaluminophosphate molecular sieve catalysts for the instant process is preferably related, in part, to the desired product mixture sought to be obtained. The selected silicoaluminophosphate molecular sieve desirably has a kinetic pore diameter (average kinetic diameter in Angstroms, Å) such that the selectivity to the light olefin products is greater than 50 molar percent. Accordingly, at least a portion, preferably a major portion, of the pores have an average kinetic diameter characterized such that the adsorption capacity (as measured by the standard McBain-Bakr gravimetric adsorption method using given adsorbate molecules) shows absorption of oxygen (average kinetic diameter of about 3.46 Å) and negligible adsorption of isobutane (average kinetic diameter of about 5.0 Å). More preferably the average kinetic diameter is characterized by adsorption of xenon (average kinetic diameter of about 4.0 Å) and negligible adsorption of isobutane and most preferably by adsorption of n-hexane (average kinetic diameter of about 4.3 Å) and negligible adsorption of isobutane. Negligible adsorption of oxygen or xenon is adsorption of less than four percent by weight of the adsorbate based on the weight of the silicoaluminophosphate and adsorption of oxygen or xenon is adsorption of greater than or equal to four percent by weight of the adsorbate based on the weight of the silicoaluminophosphate. Negligible adsorption of n-hexane or isobutane is adsorption of less than two percent by weight of the adsorbate based on the weight of the silicoaluminophosphate and adsorption of n-hexane or isobutane is adsorption of greater than or equal to two percent by weight of the adsorbate based on the weight of the silicoaluminophosphate. Although it is clear that factors other than just the kinetic pore size will affect the products formed, including any occlusion of the pores, the exact nature of such other factors or their exact effect on the products formed are not understood at present. It is believed that the kinetic diameter of the pores of the silicoaluminophosphate molecular sieve is related to the products formed. Although a specific silicoaluminophosphate may not have a kinetic pore diameter within the desired or preferred range the silicoaluminophosphate may be modified by depositing or impregnating such with cations, anions, salts and/or compounds that occlude or otherwise result in the modification of a silicoaluminophosphate having a large pore size to one having a kinetic pore diameter(s) within the desired or preferred range.

Techniques which may be employed to effect the diminution of the pore size of a silicoaluminophosphate molecular sieve are generally known in the art. Such procedures generally involve the introduction to a pore of a pore size restricting material and may involve such procedures as (1) impregnating the silicoaluminophosphate with a solution comprising a solvent or solubilizing agent for such a pore restricting material (one or more) in an amount sufficient to deposit the desired weight of such pore restricting material to the silicoaluminophosphate such that the desired pore size is obtained, and/or (2) exchanging the silicoaluminophosphate with a solution containing the pore size restricting material. The impregnation or deposition of the pore restricting materials may be generally accomplished by heating the silicoaluminophosphate at an elevated temperature to evaporate any liquid present to effect deposition or impregnation of the pore restricting material into the interior and/or onto the exterior surface of the silicoaluminophosphate, or by the exchange of cations present in the silicoaluminophosphate with cations that provide for the desired kinetic pore size. Alternatively, the pore restricting material may be formed on the silicoaluminophosphate from an emulsion or slurry containing the pore restricting material by heating the silicoaluminophosphate as described above. Impregnation and exchange procedures are generally the preferred techniques because they utilize and introduce the pore restricting material more efficiently than other procedures such as coating procedures since a coating procedure is generally not able to effect substantial introduction of the pore restricting material onto the interior surfaces of the silicoaluminophosphate. In addition, coated materials are more generally susceptible to the loss of the pore restricting materials by abrasion.

Suitable pore restricting materials include alkali metal, alkaline earth metals, transition metals and the salts thereof including inorganic and organic salts such as: nitrates, halides, hydroxides, sulfates and carboxylates. Other pore restricting materials generally employed in the art for such are also believed to be employable herein.

In carrying out the instant process the silicoaluminophosphate molecular sieves may be admixed (blended) or provided sequential to other materials which may provide some property which is beneficial under process conditions, such as improved temperature resistance or improved catalyst life by minimization of coking or which is simply inert under process conditions. Such materials may include synthetic or naturally occurring substances as well as inorganic materials such as clays, silicas, aluminas, crystalline aluminosilicate zeolites, metal oxides and mixtures thereof. In addition, the silicoaluminophosphate molecular sieves may be formed with materials such as silica, alumina, silica-alumina, silica-magnesia, silica-zirconia, silica-thoria, silica-berylia, silica-titania, as well as ternary compositions, such as silica-alumina-thoria, silica-alumina-zirconia and clays present as binders. The relative proportions of the above materials and the silicoaluminophosphate may vary widely with silicoaluminophosphate content ranging between about 1 and about 99 percent by weight of the composite.

Silicoaluminophosphate molecular sieves employable in the instant process will be referred to hereinafter, solely for point of reference herein, as "SAPO" molecular sieves, or as "SAPOs" if the reference is to the class as a whole as employed herein. This designation is simply made for the sake of convenient reference herein and is not meant to designate a particular structure for any given silicoaluminophosphate (SAPO) molecular sieve. Although, the class of SAPO's employable in the instant process is that class which will produce $C_2$, $C_3$ and/or $C_4$ olefins from the feedstock at a sufficient temperature and related process conditions. The class of SAPO's described in U.S. Pat. No. 4,440,871, said U.S. patent being incorporated herein by reference thereto, is particularly well suited for use in the present process. The members of the class of SAPO's employed hereinafter in the examples will be characterized simply by referring to such members as SAPO-5, SAPO-11, etc, i.e., a particular species will be referred to as SAPO-n where "n" is a number specific to a given class member as its preparation is reported herein. This designation is an arbitrary one and is not intended to denote structure or relationship to another material(s) which may also be characterized by a numbering system.

The silicoaluminophosphates of U.S. Pat. No. 4,440,871 are generally described as microporous crystalline silicoaluminophosphates the pores of which are uniform and have nominal diameters of greater than about 3 Angstroms and whose essential empirical chemical composition in the as-synthesized and anhydrous form is

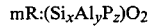

wherein "R" represents at least one organic templating agent present in the intracrystalline pore system; "m" has a value of from 0.02 to 0.3; "m" represents the moles of "R" present per mole of $(Si_xAl_yP_z)O_2$; "x", "y" and "z" represent the mole fractions of silicon, aluminum and phosphorus respectively, present as tetrahedral oxides, said mole fractions being such that they are within the pentagonal compositional area defined by points A, B, C, D and E of the ternary diagram which is FIG. 1 of the drawings of U.S. Pat. No. 4,440,871, incorporated herein by reference thereto and designated herein as FIG. 1 as well. The silicoaluminophosphates of U.S. Pat. No. 4,440,871 are further characterized by characteristic x-ray powder diffraction patterns as set forth in Tables I, III, V, VII, IX, XI, XIII, XV, SVII, XIX, XXI, XXIII, and XXV, said tables being incorporated herein by reference thereto. U.S. Pat. No. 4,440,871 further characterizes the silicoaluminophosphate materials as having three-dimensional microporous framework structure of $PO_2^+$, $AlO_2^-$ and $SiO_2$ tetrahedral units, and whose essential empirical chemical composition on an anhydrous basis is:

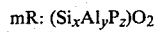

wherein R represents at least one organic templating agent present in the intracrystalline pore system; "m" represents the moles of "R" present per mole of $(Si_xAl_yP_z)O_2$ and has a value of from zero to 0.3; "x", "y" and "z" represent respectively, the mole fractions of silicon, aluminum and phosphorus present in the oxide moiety, said mole fractions being within the compositional area bounded by points A, B, C, D and E on the ternary diagram which is FIG. 1, said silicoaluminophosphate having a characteristic x-ray powder diffraction pattern which contains at least the d-spacings set forth below in any one of Tables I, III, V, VII, IX, XIII, XVIII, XXI, XXIII or XXV, of U.S. Pat. No. 4,440,871 which are reproduced hereinbelow. It will be noticed that the SAPO's having such d-spacings fit for the most part within the compositional area bounded by points a, b, c, d and e on the ternary diagram which is FIG. 2. The calcined forms of the above described silicoaluminophosphates are also disclosed in U.S. Pat. No. 4,440,871.

PREPARATIONS OF USEFUL SAPO'S

SAPO-5

The species SAPO-5 as referred to herein is a silicoaluminophosphate material having a three-dimensional microporous crystal framework structure of $PO_2^+$, $AlO_2^-$ and $SiO_2$ tetrahedral units, and whose essential empirical chemical composition on an anhydrous basis is:

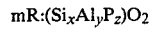

wherein "R" represents at least one organic templating agent present in the intracrystalline pore system; "m" represents the moles of "R" present per mole of $(Si_xAl_yP_z)O_2$ and has a value of from zero to 0.3, "x", "y" and "z" represent respectively, the mole fractions of silicon, aluminum and phosphorus present in the oxide moiety, said mole fractions being within the compositional area bounded by points A, B, C, D and E on the ternary diagram which is FIG. 1, or preferably within the area bounded by points a, b, c, d and e on the ternary diagram which is FIG. 2, said silicoaluminophosphate having a characteristic X-ray powder diffraction pattern which contains at least the d-spacings set forth below in Table I. In the form as synthesized in accordance with the process of this invention, "m" has a value of from 0.02 to 0.3.

TABLE I

| 2θ | d | Relative Intensity |
|---|---|---|
| 7.35–7.65 | 12.0–11.56 | m–vs |
| 19.6–19.95 | 4.53–4.46 | m |
| 20.9–21.3 | 4.25–4.17 | m–vs |
| 22.3–22.6 | 3.99–3.93 | m–vs |
| 25.85–26.15 | 3.46–3.40 | w–m |

All of the as-synthesized SAPO-5 compositions for which X-ray powder diffraction data have presently been obtained have patterns which are within the generalized pattern of Table II below:

TABLE II

| 2θ | d | 100 × I/I$_o$ |
|---|---|---|
| 7.35–7.65 | 12.0–11.56 | 52–100 |
| 12.75–13.1 | 6.94–6.76 | 7–18 |
| 14.8–15.1 | 5.99–5.91 | 13–25 |
| 19.6–19.95 | 4.53–4.47 | 31–56 |
| 20.9–21.3 | 4.25–4.17 | 30–100 |
| 22.3–22.6 | 3.99–3.93 | 44–100 |
| 24.6–24.8 | 3.62–3.59 | 2–5 |
| 25.8–26.15 | 3.453–3.408 | 19–37 |
| 28.9–29.25 | 3.089–3.053 | 8–21 |
| 29.9–30.25 | 2.998–2.954 | 11–22 |
| 33.3–33.85 | 2.691–2.648 | 2–5 |
| 34.4–34.8 | 2.607–2.578 | 9–16 |
| 36.8–37.2 | 2.442–2.417 | 2–3 |
| 37.5–37.9 | 2.398–2.374 | 6–13 |
| 40.6–41.0 | 2.222–2.201 | 0–1 |
| 41.4–41.8 | 2.181–2.161 | 1–3 |
| 42.1–42.4 | 2.146–2.132 | 2–5 |
| 42.6–42.9 | 2.122–2.108 | 1–4 |
| 43.5–43.6 | 2.080–2.076 | 1–3 |
| 44.9–45.0 | 2.019–2.014 | 0–3 |
| 47.55–48.1 | 1.912–1.892 | 3–8 |
| 51.4–51.65 | 1.778–1.773 | 0–2 |
| 51.8–52.1 | 1.765–1.755 | 0–2 |
| 55.4–55.8 | 1.658–1.647 | 1–4 |

It will be noted in the case of SAPO-5 that the essential d-spacings of Table I are common to the X-ray patterns of all of the as-synthesized forms, i.e., template-containing, and those calcined forms of SAPO-5 which contain no templating agent. It has been found, however, that in the case of the X-ray patterns of several other SAPO species, there can be an apparent substantial difference in the position and intensities of certain d-spacings between the as-synthesized and the calcined form. These differences are not believed to be indicative of a fundamental structure change as a consequence of calcination, but rather indicate a relaxation of lattice distortion caused by the presence of organic templating agents in the intracrystalline pore system which are too large to be accommodated without some bond-stretching within the SAPO crystal lattice. Upon calcination, the removal of the organic species by thermal destruction permits the structure to relax to its normal condition. Thus it may be possible to utilize a templating agent in the preparation of SAPO-5 or any SAPO species of this invention which is large enough to change the position of one or more d-spacings with respect to the X-ray patterns presented in this application for such species while not creating a distinct silicoaluminophosphate crystal structure.

Preparation 1

A reaction mixture was prepared by combining 7.69 grams of 85 wt.% orthophosphoric acid (H$_3$PO$_4$) and 33.29 grams of water, to which was added 4.58 grams of a hydrated aluminum oxide (a pseudo-boehmite phase, 74.2 wt.% Al$_2$O$_3$, 25.8 wt.% H$_2$O), and stirred until homogeneous. To this mixture was first added 1.08 gram of 37 wt.% HCl, and then 2.16 grams of a fumed silica (92.8 wt.% SiO$_2$, 7.2 wt.% H$_2$O) and the mixture stirred until homogeneous. Finally there was added 16.30 grams of an aqueous solution of 40 wt.% tetraethylammonium hydroxide (TEAOH) and the mixture stirred until homogeneous. The composition of the final reaction mixture in molar oxide ratios was:

Al$_2$O$_3$:P$_2$O$_5$:0.665(TEA)$_2$O:SiO$_2$:0.33HCl:80H$_2$O in terms of molar proportions in which the silicon, aluminum and phosphorus sources are expressed as TO$_2$, i.e., (Si$_x$Al$_y$P$_z$)O$_2$ units, the reaction mixture can be expressed as:

0.27(TEA):(Si$_{0.20}$Al$_{0.40}$P$_{0.40}$)O$_2$:16H$_2$O

A portion of this reaction mixture was sealed in a stainless steel pressure vessel lined with polytetrafluoroethylene and heated in an oven at 150° C. at autogenous pressure for 168 hours. The solid reaction product was recovered by filtration, washed with water, and dried in air overnight at room temperature. The composition of the as-synthesized solid product was determined in accordance with the law of mass balance using data from the chemical analysis of the mother liquor, specifically:

| | |
|---|---|
| Al$_2$O$_3$ | 0.94 mgs./ml |
| P$_2$O$_5$ | 24.6 mgs./ml |
| SiO$_2$ | 1.11 mgs./ml |
| Na$_2$O | 0.15 mgs./ml |
| C | 65 mgs./ml |
| N | 9.3 mgs./ml |
| Cl | 7.2 mgs./ml |

The (TEA)$_2$O content was calculated from the carbon analysis, and the H$_2$O content was determined by difference. The as-synthesized composition, denominated SAPO-5, thus had a chemical composition (anhydrous basis):

0.05(TEA).(Si$_{0.22}$Al$_{0.45}$P$_{0.33}$)O$_2$

The chemical composition in terms of mole ratios of oxides was:

0.985Al$_2$O$_3$:0.716P$_2$O$_5$:0.97SiO$_2$:0.109(TEA)$_2$O.

A portion of the solids was analyzed chemically and found to contain 6.9 wt.-% C, 1.0 wt.-% N, 16.3 wt.-% SiO$_2$, 28.9 wt.-% Al$_2$O$_3$, 38.3 wt.-% P$_2$O$_5$ and 14.4 LOI, giving a product composition in molar oxide ratios of:

1.0Al$_2$O$_3$:0.95P$_2$O$_5$:0.96SiO$_2$:0.13(TEA)$_2$O:0.8H$_2$O which corresponds to the formula (anhydrous basis):

0.053(TEA).(Si$_{0.2}$Al$_{0.41}$P$_{0.39}$)O$_2$

The X-ray powder diffraction pattern of the SAPO-5 product was characterized by the following data:

TABLE A

| 2θ | d | 100 × I/I$_o$ |
|---|---|---|
| 7.5 | 11.8 | 100 |
| 12.9 | 6.86 | 12 |
| 15.0 | 5.91 | 26 |
| 19.9 | 4.46 | 61 |

TABLE A-continued

| $2\theta$ | d | $100 \times I/I_o$ |
|---|---|---|
| 21.1 | 4.21 | 53 |
| 22.45 | 3.96 | 77 |
| 24.8 | 3.59 | 5 |
| 26.0 | 3.43 | 30 |
| 29.1 | 3.07 | 17 |
| 30.15 | 2.96 | 19 |
| 33.65 | 2.66 | 5 |
| 34.65 | 2.59 | 16 |

This X-ray pattern and all other X-ray patterns appearing hereinafter were obtained using standard X-ray powder diffraction techniques. The radiation source was a high-intensity, copper target, X-ray tube operated at 50 Kv and 40 ma. The diffraction pattern from the copper $K^\alpha$ radiation and graphite monochromator is suitably recorded by an X-ray spectrometer scintillation counter, pulse height analyzer and strip chart recorder. Flat compressed powder samples are scanned at 2° (2 theta) per minute, using a two second time constant. Interplanar spacings (d) in Angstrom units are obtained from the position of the diffraction peaks expressed as $2\theta$ where $\theta$ is the Bragg angle as observed on the strip chart. Intensities were determined from the heights of diffraction peaks after subtracting background, "$I_o$" being the intensity of the strongest line or peak, and "I" being the intensity of each of the other peaks.

As will be understood by those skilled in the art the determination of the parameter 2 theta is subject to both human and mechanical error, which in combination, can impose an uncertainty of about ±0.4° on each reported value of 2 theta. This uncertainty is, of course, also manifested in the reported values of the d-spacings, which are calculated from the 2 theta values. This imprecision is general throughout the art and is not sufficient to preclude the differentiation of the present crystalline materials from each other and from the compositions of the prior art. In some of the X-ray patterns reported, the relative intensities of the d-spacings are indicated by the notations vs, s, m, w and vw which represent very strong, strong, medium, weak and very weak, respectively.

Preparation 2

(a) A reaction mixture was prepared by combining 18.44 grams of 85 wt. % orthophosphoric acid ($H_3PO_4$) and 11.56 grams of water, to which was added 11.04 grams of hydrated aluminum oxide (a pseudo-boehmite phase, 74.2 wt. % $Al_2O_3$, 25.8 wt. % $H_2O$), and stirred until homogeneous. To this mixture was added a dispension of 2.08 grams of a fumed silica (92.8 wt. % $SiO_2$, 7.2 wt. % $H_2O$), in 81.64 grams of an aqueous solution of 40% tetra-n-propylammonium hydroxide (TPAOH), and the mixture stirred until homogeneous. The composition of the final reaction mixture in molar oxide ratios was:

$Al_2O_3:P_2O_5:0.4SiO_2:(TPA)_2O:50H_2O$

A portion of the reaction mixture was sealed in a stainless steel pressure vessel lined with an inert plastic material and heated in an oven at 225° C. at autogenous pressure for 24 hours. The solid reaction product was recovered by centrifuging and washing with water, and dried in air at room temperature. The above product has an X-ray powder diffraction pattern characterized by the following data:

TABLE C

| $2\theta$ | d | $100 \times I/I_o$ |
|---|---|---|
| 7.4 | 11.95 | 100 |
| 12.9 | 6.86 | 11 |
| 14.9 | 5.95 | 25 |
| 19.7 | 4.51 | 51 |
| 21.1 | 4.21 | 67 |
| 22.3 | 3.99 | 92 |
| 24.8 | 3.59 | 5 |
| 25.8 | 3.453 | 37 |
| 28.9 | 3.089 | 21 |
| 29.9 | 2.988 | 22 |
| 33.6 | 2.667 | 5 |
| 34.4 | 2.607 | 16 |
| 36.8 | 2.442 | 3 |
| 37.6 | 2.392 | 9 |
| 41.5 | 2.176 | 3 |
| 42.2 | 2.141 | 5 |
| 42.8 | 2.113 | 3 |
| 43.5 | 2.080 | 3 |
| 44.9 | 2.019 | 3 |
| 47.6 | 1.910 | 8 |

Chemical analysis established that the solids (product) comprised 8.0 wt. % C, 0.97 wt. % N, 7.22 wt. % $SiO_2$, 33.5 wt. % $Al_2O_3$, 44.5 wt. % $P_2O_5$, 12.8 wt. % LOI, giving a product composition in terms of molar oxide ratios of:

$0.085(TPA)_2O:0.37SiO_2:1.0Al_2O_3:0.96P_2O_5:0.26H_2O$

In terms of moles of organic constituent per average mole of $TO_2$ units, the composition was (anhydrous basis):

$0.040(TPA):(Si_{0.08}Al_{0.47}P_{0.45})O_2$ (b) A portion of solid crystalline product was calcined in air at about 600° C. for 1 hour. The calcined product had an X-ray powder diffraction pattern characterized by the following data:

TABLE D

| $2\theta$ | d | $100 \times I/I_o$ |
|---|---|---|
| 7.5 | 11.79 | 100 |
| 13.0 | 6.81 | 27 |
| 15.0 | 5.91 | 11 |
| 19.9 | 4.46 | 42 |
| 21.3 | 4.17 | 62 |
| 22.6 | 3.93 | 96 |
| 25.0 | 3.56 | 4 |
| 26.0 | 3.427 | 44 |
| 29.2 | 3.058 | 23 |
| 30.2 | 2.959 | 23 |
| 33.8 | 2.652 | 6 |
| 34.6 | 2.592 | 17 |

(c) Adsorption capacities were measured on the calcined product of part (b), supra using a standard McBain-Bakr gravimetric adsorption apparatus. The following data were obtained on a sample activated at 350° C.

| | Kinetic Diameter, A | Pressure, Torr | Temp., °C. | Wt. % Adsorbed |
|---|---|---|---|---|
| $O_2$ | 3.46 | 100 | −183 | 14.5 |
| $O_2$ | 3.46 | 750 | −183 | 19.8 |
| Cyclohexane | 6.0 | 60 | 24 | 10.9 |
| Neopentane | 6.2 | 743 | 24 | 7.6 |
| $H_2O$ | 2.65 | 4.6 | 24 | 14.7 |
| $H_2O$ | 2.65 | 20.0 | 24 | 31.3 |

The pore size of the calcined product is greater than 6.2 A, as shown by adsorption of neopentane, kinetic diameter of 6.2 A.

(d) Ion-exchange studies were carried out on 1.0 gram of the product of part (a) calcined in air for 2 hours at 600° C. The sample was stirred at room temperature for 10 minutes with 25 cc of a saturated NaCl solution containing 1.0 gram of NaHCO$_3$. After being washed with 1 liter of hot water and then 1 liter of cold water, the product was dried in air at 100° C. for 2 hours. Chemical analysis of the product showed 29.5 wt. % Al$_2$O$_3$, 39.0 wt. % P$_2$O$_5$, 7.6 wt. % SiO$_2$, 3.3 wt. % Na$_2$O corresponding to a product composition in molar oxide ratios of 1.0Al$_2$O$_3$:0.95P$_2$O$_5$:0.44SiO$_2$:0.18Na$_2$O

SAPO-11

The species SAPO-11 as referred to herein is a silicoaluminophosphate material having a three-dimensional microporous crystal framework structure of PO$_2$$^+$, AlO$_2$$^-$ and SiO$_2$ tetrahedral units, and whose essential empirical chemical composition on an anhydrous basis is:

mR:(Si$_x$Al$_y$P$_z$)O$_2$ wherein "R" represents at least one organic templating agent present in the intracrystalline pore system; "m" represents the moles of "R" present per mole of (Si$_x$Al$_y$P$_z$)O$_2$ and has a value from zero to 0.3, "x", "y" and "z" represent respectively, the mole fractions of silicon, aluminum and phosphorus present in the oxide moiety, said mole fractions being within the compositional area bounded by points A, B, C, D and E on the ternary diagram which is FIG. 1 or preferably within the area bounded by points a, b, c, d and e on the ternary diagram which is FIG. 2, said silicoaluminophosphate having a characteristic X-ray powder diffraction pattern which contains at least the d-spacings set forth below in Table III. In the form as synthesized in accordance with the process of this invention, "m" has a value of from 0.02 to 0.3.

TABLE III

| 2θ | d | Relative Intensity |
|---|---|---|
| 9.4–9.65 | 9.41–9.17 | m |
| 20.3–20.6 | 4.37–4.31 | m |
| 21.0–21.3 | 4.23–4.17 | vs |
| 22.1–22.35 | 4.02–3.99 | m |
| 22.5–22.9 (doublet) | 3.95–3.92 | m |
| 23.15–23.35 | 3.84–3.81 | m–s |

All of the as-synthesized SAPO-11 compositions for which X-ray powder diffraction data have presently been obtained have patterns which are within the generalized pattern of the Table IV below.

TABLE IV

| 2θ | | d | 100 × I/I$_o$ |
|---|---|---|---|
| 8.05–8.3 | | 10.98–10.65 | 20–42 |
| 9.4–9.65 | | 9.41–9.17 | 36–58 |
| 13.1–13.4 | | 6.76–6.61 | 12–16 |
| 15.6–15.85 | | 5.68–5.59 | 23–38 |
| 16.2–16.4 | | 5.47–5.40 | 3–5 |
| 18.95–19.2 | | 4.68–4.62 | 5–6 |
| 20.3–20.6 | | 4.37–4.31 | 36–49 |
| 21.0–21.3 | | 4.23–4.17 | 100 |
| 22.1–22.35 | | 4.02–3.99 | 47–59 |
| 22.5–22.9 | (doublet) | 3.95–3.92 | 55–60 |

TABLE IV-continued

| 2θ | | d | 100 × I/I$_o$ |
|---|---|---|---|
| 23.15–23.35 | | 3.84–3.81 | 64–74 |
| 24.5–24.9 | (doublet) | 3.63–3.58 | 7–10 |
| 26.4–26.8 | (doublet) | 3.38–3.33 | 11–19 |
| 27.2–27.3 | | 3.28–3.27 | 0–1 |
| 28.3–28.5 | (shoulder) | 3.15–3.13 | 11–17 |
| 28.6–28.85 | | 3.121–3.094 | |
| 29.0–29.2 | | 3.079–3.058 | 0–3 |
| 29.45–29.65 | | 3.033–3.013 | 5–7 |
| 31.45–31.7 | | 2.846–2.823 | 7–9 |
| 32.8–33.1 | | 2.730–2.706 | 11–14 |
| 34.1–34.4 | | 2.629–2.607 | 7–9 |
| 35.7–36.0 | | 2.515–2.495 | 0–3 |
| 36.3–36.7 | | 2.475–2.449 | 3–4 |
| 37.5–38.0 | (doublet) | 2.398–2.368 | 10–13 |
| 39.3–39.55 | | 2.292–2.279 | 2–3 |
| 40.3 | | 2.238 | 0–2 |
| 42.2–42.4 | | 2.141–2.132 | 0–2 |
| 42.8–43.1 | | 2.113–2.099 | 3–6 |
| 44.8–45.2 | (doublet) | 2.023–2.006 | 3–5 |
| 45.9–46.1 | | 1.977–1.969 | 0–2 |
| 46.8–47.1 | | 1.941–1.929 | 0–1 |
| 48.7–49.0 | | 1.870–1.859 | 2–3 |
| 50.5–50.8 | | 1.807–1.797 | 3–4 |
| 54.6–54.8 | | 1.681–1.675 | 2–3 |
| 55.4–55.7 | | 1.658–1.650 | 0–2 |

Preparation 3

(a) A reaction mixture was prepared by combining 160 grams of water and 90.7 grams of aluminum isopropoxide (Al(OC$_3$H$_7$)$_3$) to which was added 51.3 grams of 85 wt. % orthophosphoric acid (H$_3$PO$_4$) and the mixture stirred well. To this was added 1.4 grams of a fumed silica (95 wt. % SiO$_2$; 5 wt. % H$_2$O) and then, after stirring, 7.4 grams of di-n-propylamine (Pr$_2$NH) was added to one-third by weight of the above mixture. The final mixture was stirred until homogeneous. The composition of the final reaction mixture in molar oxide ratios was:

1.0Pr$_2$NH:0.1SiO$_2$:Al$_2$O$_3$:P$_2$O$_5$:42H$_2$O

In terms of molar proportions in which the silicon, aluminum and phosphorus sources are expressed as TO$_2$, i.e., (Si$_x$Al$_y$P$_z$)O$_2$, units, the reaction mixture can be expressed as:

0.24(Pr$_2$NH):(Si$_{0.02}$Al$_{0.49}$Si$_{0.49}$)O$_2$:10.2H$_2$O

The reaction mixture was sealed in a stainless steel pressure vessel lined with polytetrafluoroethylene and heated in an oven at 150° C. at autogenous pressure for 133 hours. The solid reaction product was recovered by centrifugation, washed with water, and dried in air at room temperature. Chemical analysis established the composition to comprise 3.5 wt. % C, 0.65 wt. % N, 38.2 wt. % Al$_2$O$_3$, 35.9 wt. % P$_2$O$_5$, 2.9 wt. % SiO$_2$, 17.7 wt. % LOI, giving a product composition (anhydrous basis) for the SAPO-11 as follows:

0.037Pr$_2$NH:(Si$_{0.04}$Al$_{0.57}$P$_{0.39}$)O$_2$ or, in terms of mole ratios of oxides:

0.13Pr$_2$NH:Al$_2$O$_3$:0.68P$_2$O$_5$:0.13SiO$_2$:2.1H$_2$O

The as-synthesized composition had an X-ray powder diffraction pattern characterized by the following data:

TABLE F

| 2θ | d | 100 × I/I₀ |
|---|---|---|
| 8.05 | 10.98 | 20 |
| 9.4 | 9.41 | 36 |
| 13.1 | 6.76 | 13 |
| 15.65 | 5.66 | 23 |
| 16.3 | 5.44 | 3 |
| 18.95 | 4.68 | 5 |
| 20.4 | 4.35 | 36 |
| 21.0 | 4.23 | 100 |
| 22.1 | 4.02 | 54 |
| 22.5 | 3.95 | } 56 |
| 22.7 sh* | 3.92 | |
| 23.15 | 3.84 | 66 |
| 24.5 | 3.63 | } 8 |
| 24.7 | 3.60 | |
| 26.4 | 3.38 | 19 |
| 27.2 | 3.28 | 1 |
| 28.6 | 3.121 | 14 |
| 29.0 | 3.079 | 3 |
| 29.45 | 3.033 | 6 |
| 31.5 | 2.840 | 8 |
| 32.8 | 2.730 | 13 |
| 34.1 | 2.629 | 8 |
| 35.75 | 2.512 | 3 |
| 36.3 | 2.475 | 3 |
| 37.5 | 2.398 | } 10 |
| 37.8 | 2.380 | |
| 39.3 | 2.292 | 3 |
| 40.3 | 2.238 | 2 |
| 42.8 | 2.113 | 6 |
| 44.9 | 2.019 | 4 |
| 46.8 | 1.941 | 1 |
| 48.7 | 1.870 | 2 |
| 50.5 | 1.807 | 3 |
| 54.6 | 1.684 | 4 |

*sh = shoulder (b) A portion of the product of part (a) was calcined in air at 500° C. for 1 hour, then at 600° C. for 1 hour. The calcined product has an X-ray powder diffraction pattern characterized by the following data:

| 2θ | d | 100 × I/I₀ |
|---|---|---|
| 8.1 | 10.9 | 54 |
| 9.6 | 9.2 | 53 |
| 12.8 | 6.92 | } 18 |
| 13.05 | 6.78 | |
| 15.85 | 5.59 | } 46 |
| 16.1 (sh) | 5.50 | |
| 19.4 (sh) | 4.58 | } 30 |
| 20.3 | 4.37 | |
| 21.3 | 4.17 | 100 |
| 21.9 (sh) | 4.06 | 39 |
| 22.3 | 3.99 | 75 |
| 22.9 (sh) | 3.88 | 41 |
| 23.3 | 3.82 | 60 |
| 24.1 | 3.69 | 9 |
| 24.9 | 3.58 | 5 |
| 26.35 | 3.38 | 20 |
| 28.9 | 3.089 | 12 |
| 29.5 | 3.028 | 11 |
| 30.3 | 2.950 | 5 |
| 31.7 | 2.823 | 9 |
| 32.75 | 2.734 | 14 |
| 34.0 | 2.637 | 4 |
| 34.55 | 2.596 | 5 |
| 36.2 | 2.481 | 7 |
| 37.1 | 2.423 | 2 |
| 37.8 | 2.380 | 10 |
| 39.4 | 2.287 | 2 |
| 41.0 | 2.201 | 1 |
| 43.2 | 2.094 | 3 |
| 44.7 | 2.027 | 3 |
| 48.3 | 1.884 | 1 |
| 51.2 | 1.784 | 2 |

*sh = shoulder (c) Adsorption capacities were measured on this calcined product using a standard McBain-Bakr gravimetric adsorption apparatus. The following data were obtained on a sample activated at 350° C.

| | Kinetic Diameter, Å | Pressure, Torr | Temp, °C. | Wt. % Adsorbed |
|---|---|---|---|---|
| O₂ | 3.46 | 102 | −183 | 7.3 |
| O₂ | 3.46 | 743 | −183 | 15.3 |
| Cyclohexane | 6.0 | 52 | 24.6 | 6.9 |
| Neopentane | 6.2 | 300 | 24.8 | 1.7 |
| H₂O | 2.65 | 4.6 | 23.9 | 11.4 |
| H₂O | 2.65 | 20.2 | 23.2 | 18.0 |

The pore size of the calcined product is >6.0 Å and <6.2 Å as shown by adsorption of cyclohexane, kinetic diameter of 6.0 Å and negligible adsorption of neopentane, kinetic diameter of 6.2 Å.

SAPO-16

The species SAPO-16 as referred to herein is a silicoaluminophosphate material having a three-dimensional microporous crystal framework structure of $PO_2^+$, $AlO_2^-$ and $SiO_2$ tetrahedral units, and whose essential empirical chemical composition on an anhydrous basis is:

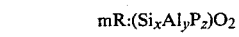

$$mR:(Si_xAl_yP_z)O_2$$

wherein "R" represents at least one organic templating agent present in the intracrystalline pore system; "m" represents the moles of "R" present per mole of $(Si_xAl_yP_z)O_2$ and has a value of from zero to 0.3, "x", "y" and "z" represent respectively, the mole fractions of silicon, aluminum and phosphorus present in the oxide moiety, said mole fractions being within the compositional area bounded by points A, B, C, D and E on the ternary diagram which is FIG. 1, or preferably within the area bounded by points a, b, c, d and e on the ternary diagram which is FIG. 2, said silicoaluminophosphate having a characteristic X-ray powder diffraction pattern which contains at least the d-spacings set forth below in Table V. In the form as synthesized in accordance with the process of this invention, "m" has a value of from 0.02 to 0.3.

TABLE V

| 2θ | d | Relative Intensity |
|---|---|---|
| 11.3–11.5 | 7.83–7.69 | m |
| 18.7–18.9 | 4.75–4.70 | m |
| 21.9–22.3 | 4.06–3.99 | vs |
| 26.5–27.0 | 3.363–3.302 | w–m |
| 29.7–30.05 | 3.008–2.974 | w–m |

All of the as-synthesized SAPO-16 compositions for which X-ray powder diffraction data have presently been obtained have patterns which are within the generalized pattern of Table VI below.

TABLE VI

| 2θ | d | 100 × I/I_o |
|---|---|---|
| 11.3–11.5 | 7.83–7.69 | 52–66 |
| 17.0–17.5 | 5.22–5.07 | 0–4 |
| 18.7–18.9 | 4.75–4.70 | 50–58 |
| 21.9–22.3 | 4.06–3.99 | 100 |
| 26.5–27.0 | 3.363–3.302 | 15–23 |
| 29.1–29.4 | 3.069–3.038 | 5–13 |
| 29.7–30.05 | 3.008–2.974 | 23–26 |
| 32.7–32.9 | 2.739–2.722 | 0–3 |
| 34.4–34.8 | 2.607–2.578 | 2–4 |
| 38.0–38.3 | 2.368–2.350 | 7–9 |
| 39.9–40.3 | 2.259–2.238 | 0–7 |
| 44.3–44.45 | 2.045–2.038 | 0–4 |
| 48.5–48.7 | 1.877–1.870 | 6–8 |
| 49.0–49.4 | 1.859–1.845 | 0–2 |
| 52.3–52.5 | 1.749–1.743 | 0–2 |
| 54.8–54.9 | 1.675–1.672 | 0–2 |

Preparation 4

A reaction mixture was prepared by combining 46.0 grams of 85 wt. % orthophosphoric acid and 100 grams of water which was added to 81.7 grams of aluminum isopropoxide ($Al(OC_3H_7)_3$) and 5.0 grams of water and the mixture stirred well. To the above mixture were added 12.0 grams of an aqueous sol containing 30 wt. % $SiO_2$, and 5.0 additional grams of water, and the mixture stirred until homogeneous. To one-half (by weight) of this mixture were added 11.1 grams of quinuclidine, $C_7H_{13}N$, (Q) and 21.9 grams of water, and the mixture stirred until homogeneous. The composition of the final reaction mixture in molar oxide ratios was:

$$1.0Q:Al_2O_3:P_2O_5:0.3SiO_2:50H_2O$$

Part of the reaction mixture was sealed in a stainless steel pressure vessel having an inert plastic liner and heated in an oven at 200° C. at autogenous pressure for 48 hours. The solid reaction product, denominated SAPO-16, was recovered by centrifugation, washed with water, and dried in air at 100° C. X-ray analysis was performed on a portion of the solids which passed through 100 mesh sieve. The SAPO-16 product had an x-ray powder diffraction pattern characterized by the following data:

TABLE K

| 2θ | d | 100 × I/I_o |
|---|---|---|
| 11.45 | 7.73 | 54 |
| 17.35 | 5.11 | 4 |
| 18.8 | 4.72 | 51 |
| 22.05 | 4.03 | 100 |
| 26.65 | 3.345 | 20 |
| 29.2 | 3.058 | 6 |
| 29.85 | 2.993 | 25 |
| 32.7 | 2.739 | 3 |
| 34.8 | 2.578 | 4 |
| 38.05 | 2.365 | 8 |
| 39.9 | 2.259 | 3 |
| 44.4 | 2.040 | 2 |
| 48.5 | 1.877 | 6 |
| 49.0 | 1.859 | 1 |
| 52.4 | 1.746 | 2 |
| 54.8 | 1.675 | 2 |

Preparation 5

A reaction mixture was prepared by combining 132 grams of water and 132.8 grams of aluminum isopropoxide ($Al(OC_3H_7)_3$) to which was added 45.0 grams of water and 30.1 grams of an aqueous sol containing 30 wt. % $SiO_2$, and the mixture stirred well. To this mixture was added 57.7 grams of 85 wt. % orthophosphoric acid, and the mixture stirred until homogeneous. To this mixture were added an aqueous solution containing 27.8 grams of quinuclidine, $C_7H_{13}N$, (Q) and 45 grams of water, and then 5 additional grams of water, and the mixture stirred until homogeneous. The composition of the final reaction mixture in molar oxide ratios was:

$$1.0Q:1.3Al_2O_3:P_2O_5:0.6SiO_2:60H_2O$$

Part of the reaction mixture was sealed in a stainless steel pressure vessel lined with polytetrafluoroethylene and heated in an oven at 200° C. at autogenous pressure for 338 hours. The solid reaction product was recovered by centrifugation, washed with water, and dried in air at 100° C. The SAPO-16 product had an X-ray powder diffraction pattern essentially identical to that in Preparation 4. By chemical analysis, the composition of the SAPO-16 product was found to be 12.2 wt. % C, 1.9 wt. % N, 7.8 wt. % $SiO_2$, 34.6 wt. % $Al_2O_3$, 32.1 wt. % $P_2O_5$, 24.6 wt. % LOI, corresponding to the formula (anhydrous basis)

$$0.116\ \text{Quinuclidine}:(Si_{0.10}Al_{0.54}P_{0.36})O_2$$

In terms of mole ratios of oxides, the composition was:

$$0.215Q_2O:Al_2O_3:0.38SiO_2:0.67P_2O_5:1.4H_2O$$

SAPO-17

The species SAPO-17 as referred to herein is a silicoaluminophosphate material having a three-dimensional microporous crystal framework structure of $PO_2^+$, $AlO_2^-$ and $SiO_2$ tetrahedral units, and whose essential empirical chemical composition on an anhydrous basis is:

$$mR:(Si_xAl_yP_z)O_2$$

wherein "R" represents at least one organic templating agent present in the intracrystalline pore system; "m" represents the moles of "R" present per mole of $(Si_xAl_yP_z)O_2$ and has a value of from zero to 0.3, "x", "y" and "z" represent respectively, the mole fractions of silicon, aluminum and phosphorous present in the oxide moiety, said mole fractions being within the compositional area bounded by points A, B, C, D and E on the ternary diagram which is FIG. 1, or preferably within the area bounded by points a, b, c, d and e on the ternary diagram which is FIG. 2, said silicoaluminophosphate having a characteristic X-ray powder diffraction pattern which contains at least the d-spacings set forth below in Table VII. In the form as synthesized in accordance with the process of this invention, "m" has a value of from 0.02 to 0.30.

TABLE VII

| 2θ | d | Relative Intensity |
|---|---|---|
| 7.70–7.75 | 11.5–11.4 | vs |
| 13.4 | 6.61 | s–vs |
| 15.5–15.55 | 5.72–5.70 | s |
| 19.65–19.7 | 4.52–4.51 | w–m |
| 20.5–20.6 | 4.33–4.31 | vs |
| 31.85–32 | 2.810–2.797 | w–m |

All of the as-synthesized SAPO-17 compositions for which X-ray powder diffraction data have presently been obtained have patterns which are within the generalized pattern of Table VIII below.

TABLE VIII

| $2\theta$ | d | $100 \times I/I_o$ |
|---|---|---|
| 7.70 | 11.5-11.45 | 100 |
| 9.8 | 9.03 | 5-36 |
| 11.8 | 7.50 | 1 |
| 13.4 | 6.61 | 60-95 |
| 14.2 | 6.24 | 6 |
| 15.5 | 5.72-5.70 | 37-65 |
| 16.6 | 5.34 | 19 |
| 18.0 | 4.93 | 18-25 |
| 19.65-19.7 | 4.52-4.51 | 10-39 |
| 20.5-20.6 | 4.33-4.31 | 80-100 |
| 21.4(sh) | 4.15 | |
| 22.5 | 3.95 | 7 |
| 23.3-23.4 | 3.82-3.80 | 20-38 |
| 23.8 | 3.74 | 32 |
| 25.4 | 3.507 | 15-38 |
| 27.0 | 3.302 | 25-49 |
| 27.4 | 3.255 | 5-9 |
| 28.7 | 3.110 | 5-18 |
| 30.6(sh) | 2.921 | sh-5 |
| 31.3-31.35 | 2.858-2.853 | 10-20 |
| 31.85-32.0 | 2.810-2.797 | 20-48 |
| 33.4-33.55 | 2.683-2.671 | 5-19 |
| 35.9-36.05 | 2.501-2.491 | 8-10 |
| 36.4-36.45 | 2.468-2.465 | 4-10 |
| 40.3 | 2.238 | 1 |
| 43.7 | 2.071 | 11 |
| 45.9 | 1.977 | 5 |
| 49.6-49.7 | 1.838-1.834 | 5-15 |
| 52.0-52.3 | 1.704-1.749 | 10-15 |
| 53.8-53.9 | 1.704-1.701 | 2-5 |
| 55.45-55.5 | 1.657-1.656 | 5-11 |

Preparation 6

SAPO-17 was crystallized from a reaction mixture formed by combining 57.7 grams of 85 wt. % orthophosphoric acid and 130.0 grams of water with 132.8 grams of aluminum isopropoxide (Al(OC$_3$H$_7$)$_3$) and mixing well. To this mixture were added 47.0 grams of water and 30.1 grams of an aqueous sol containing 30 wt. % SiO$_2$, and the mixture stirred until homogeneous. To this mixture was added a solution of 27.8 grams of quinuclidine, C$_7$H$_{13}$N, (Q) in 50.0 grams of water, and the mixture stirred until homogeneous. The composition of the final reaction mixture in molar oxide ratios was:

Q:0.6SiO$_2$:1.3Al$_2$O$_3$:P$_2$O$_5$:60H$_2$O

Part of the reaction mixture was placed in a stainless steel pressure vessel lined with an inert plastic material and heated in an oven at 200° C. at autogenous pressure for 338 hours. The solid reaction product was recovered by centrifugation, washed with water, and dried in air at 100° C. The SAPO-17 product was impure but the minor phase had an X-ray powder diffraction pattern characterized by the following data:

TABLE L

| $2\theta$ | d | $100 \times I/I_o$ |
|---|---|---|
| 7.75* | 11.4 | 100 |
| 9.8 | 9.03 | 5 |
| 13.4* | 6.61 | 60 |
| 15.55* | 5.70 | 65 |
| 16.7 | 5.31 | 5 |
| 18.0 | 4.93 | 25 |
| 19.7 | 4.51 | 10 |
| 20.6* | 4.31 | 100 |
| 21.4 (sh) | 4.15 | |
| 23.4 | 3.80 | 20 |
| 25.4 | 3.507 | 15 |
| 27.0 | 3.302 | 24 |
| 27.4 | 3.255 | 5 |
| 28.7 | 3.110 | 5 |
| 30.6 (sh) | 2.921 | |
| 31.35 | 2.853 | 10 |
| 32.0 | 2.797 | 20 |
| 33.4 | 2.683 | 5 |
| 36.05 | 2.491 | 10 |
| 36.45 | 2.465 | 10 |
| 40.0** | 2.254 | 40 |
| 40.3** | 2.238 | |
| 45.9 | 1.977 | 5 |
| 49.7 | 1.834 | 5 |
| 52.3** | 1.749 | 15 |
| 53.9 | 1.701 | 5 |
| 55.5 | 1.656 | 5 |

*probably contains peak from another phase
**contains peak from another phase

Preparation 7

(a) A substantially purer SAPO-17 composition was prepared using cyclohexylamine (instead of the quinuclidine of Prep. 6 supra) as the templating agent and decreasing the relative proportion of silica in the gel. This superior reaction mixture was prepared by combining 81.7 grams of aluminum isopropoxide [Al(OC$_3$H$_7$)$_3$)] with a solution of 46.1 grams of 85 wt. % orthophosphoric acid (H$_3$PO$_4$) in 159.6 grams of H$_2$O, stirring until homogeneous, and then adding 4.0 grams of an aqueous silica sol containing 30 wt.-% SiO$_2$. The resulting mixture was stirred until it was homogeneous. To this mixture was added 19.8 grams of cyclohexylamine (CHA), and the mixture stirred until homogeneous. The composition of the final reaction mixture in molar oxide ratios was:

1.0CHA:0.1SiO$_2$:Al$_2$O$_3$:P$_2$O$_5$:50H$_2$O

A portion of the reaction mixture was sealed in a stainless steel pressure vessel lined with polytetrafluoroethylene and heated in an oven at 200° C. at autogenous pressure for 50 hours. The solid reaction product was recovered by filtration, washed with water, and dried in air at 100° C. By chemical analysis, the composition of the product was found to be 9.5 wt.-% C; 1.6 wt.-% SiO$_2$; 37.8 wt.-% Al$_2$O$_3$; 39.9 wt.-% P$_2$O$_5$ and 19.8 wt.-% LOI, corresponding to the formula (anhydrous basis):

0.103CHA:(Si$_{0.02}$Al$_{0.56}$P$_{0.42}$)O$_2$, or in terms of molar oxide ratios:

0.18(CHA)$_2$O:Al$_2$O$_3$:0.76P$_2$O$_5$:0.07SiO$_2$

The SAPO-17 product was impure and had an X-ray powder diffraction pattern characterized by the following data:

TABLE M

| $2\theta$ | d | $100 \times I/I_o$ |
|---|---|---|
| 7.7 | 11.5 | 100 |
| 9.8 | 9.03 | 36 |
| 10.9* | 8.12 | 9 |
| 11.8 | 7.50 | 1 |
| 13.4** | 6.61 | 95 |
| 14.2 | 6.24 | 6 |
| 15.5 | 5.72 | 37 |
| 16.6 | 5.34 | 19 |
| 17.4* | 5.10 | 8 |
| 18.0 | 4.93 | 18 |
| 19.65 | 4.52 | 39 |

TABLE M-continued

| $2\theta$ | d | $100 \times I/I_o$ |
|---|---|---|
| 20.5 | 4.33 | 80 |
| 21.4** | 4.15 | 35 |
| 22.0* | 4.04 | 16 |
| 22.5 | 3.95 | 7 |
| 23.3** | 3.82 | 38 |
| 23.8 | 3.74 | 32 |
| 25.4 | 3.507 | 38 |
| 27.0** | 3.302 | 49 |
| 27.4 | 3.255 | 9 |
| 28.7** | 3.110 | 18 |
| 30.6 | 2.921 | 5 |
| 31.3 | 2.858 | 20 |
| 31.85 | 2.810 | 48 |
| 32.2* | 2.780 | sh |
| 33.55 | 2.671 | 19 |
| 34.6* | 2.592 | 1 |
| 35.9** | 2.501 | 8 |
| 36.4 | 2.468 | 4 |
| 37.4 | 2.404 | 2 |
| 37.9 | 2.374 | 2 |
| 39.8 | 2.265 | 3 |
| 40.3 | 2.238 | 1 |
| 40.9 | 2.206 | 1 |
| 42.1 | 2.146 | 2 |
| 42.6 | 2.122 | 1 |
| 43.7 | 2.071 | 11 |
| 45.6 | 1.989 | 1 |
| 46.5 | 1.953 | 2 |
| 47.8 | 1.903 | 1 |
| 48.7 | 1.870 | 1 |
| 49.3 | 1.848 | sh |
| 49.6 | 1.838 | 15 |
| 52.0 | 1.759 | 10 |
| 53.8 | 1.704 | 2 |
| 55.45 | 1.657 | 11 |

**contains peak from another phase
*Peak from another phase (b) The product was calcined for 4 hours at 550° C. in air. The calcined product has an X-ray powder diffraction pattern characterized by the following data (known impurity peaks have been omitted):

TABLE N

| $2\theta$ | d | $100 \times I/I_o$ |
|---|---|---|
| 7.7 | 11.5 | 92 |
| 9.65 | 9.17 | 32 |
| 11.5 | 7.69 | 10 |
| 13.5* | 6.56 | 100 |
| 13.9 | 6.37 | 21 |
| 15.6 | 5.68 | 11 |
| 16.65 | 5.32 | 22 |
| 19.0 | 4.67 | 7 |
| 19.4 | 4.58 | 6 |
| 20.7 | 4.29 | 22 |
| 21.45* | 4.14 | 13 |
| 23.5 | 3.79 | 19 |
| 23.7 | 3.75 | sh |
| 24.5 | 3.63 | 19 |
| 27.15 | 3.285 | 17 |
| 28.0 | 3.187 | 5 |
| 30.1 | 2.969 | 1 |
| 30.6 | 2.921 | 3 |
| 31.25 | 2.862 | 14 |
| 32.0 | 2.797 | 9 |
| 33.55 | 2.671 | 6 |
| 35.0 | 2.564 | 2 |
| 36.2 | 2.481 | 3 |
| 39.4 | 2.287 | 2 |
| 40.2 | 2.243 | 1 |
| 41.3 | 2.186 | 2 |
| 41.9 | 2.156 | 1 |
| 42.6 | 2.122 | 3 |
| 43.5 | 2.080 | 1 |
| 46.0 | 1.973 | 1 |
| 46.4 | 1.957 | 1 |
| 47.1 | 1.929 | 2 |
| 47.9 | 1.899 | 2 |

TABLE N-continued

| $2\theta$ | d | $100 \times I/I_o$ |
|---|---|---|
| 50.1 | 1.821 | 5 |
| 51.2 | 1.784 | 5 |
| 52.7 | 1.737 | 1 |
| 55.2 | 1.664 | 2 |

*contains peak from another phase (c) Adsorption capacities were measured on the calcined product of part (b) supra using standard McBain-Bakr gravimetric adsorption apparatus. The following data were obtained on a sample activated at 350° C.:

| | Kinetic Diameter, Å | Pressure, Torr | Temp., °C. | Wt. % Adsorbed |
|---|---|---|---|---|
| $O_2$ | 3.46 | 98.5 | −183 | 21.5 |
| $O_2$ | 3.46 | 740 | −183 | 29.4 |
| n-hexane | 4.3 | 53.5 | 24 | 10.3 |
| $H_2O$ | 2.65 | 4.6 | 23 | 25.2 |
| $H_2O$ | 2.65 | 19.4 | 24 | 35.0 | the pore size of the calcined product is >4.3 Å and <5.0 Å as shown by the adsorption of n-hexane, kinetic diameter of 4.3 Å, and negligible adsorption of isobutane, kinetic diameter of 5.0 Å.

SAPO-20

The species SAPO-20 as referred to herein is a silicoaluminophosphate material having a three-dimensional microporous crystal framework structure of $PO_2^+$, $AlO_2^-$ and $SiO_2$ tetrahedral units, and whose essential empirical chemical composition on an anhydrous basis is:

$$mR:(Si_xAl_yP_z)O_2$$

wherein "R" represents at least one organic templating agent present in the intracrystalline pore system; "m" represents the moles of "R" present per mole of $(Si_xAl_yP_z)O_2$ and has a value of from zero to 0.3, "x", "y" and "z" represent respectively, the mole fractions of silicon, aluminum and phosphorus present in the oxide moiety, said mole fractions being within the compositional area bounded by points A, B, C, D and E on the ternary diagram which is FIG. 1, or preferably within the area bounded by points a, b, c, d and e on the ternary diagram which is FIG. 2, said silicoaluminophosphate having a characteristic X-ray powder diffraction pattern which contains at least the d-spacings set forth below in Table IX. In the form as synthesized in accordance with the process of this invention, "m" has a value of from 0.02 to 0.3.

TABLE IX

| $2\theta$ | d | Relative Intensity |
|---|---|---|
| 13.7–14.25 | 6.46–6.22 | m |
| 19.55–20.0 | 4.54–4.44 | w–m |
| 24.05–24.45 | 3.700–3.641 | vs |
| 34.35–35.0 | 2.611–2.564 | w |
| 42.5–43.0 | 2.127–2.103 | vw–w |

All of the as-synthesized SAPO-20 compositions for which X-ray powder diffraction data have presently been obtained have patterns which are within the generalized pattern of Table X, below.

TABLE X

| 2θ | d | 100 × I/I₀ |
|---|---|---|
| 13.7–14.25 | 6.46–6.22 | 38–63 |
| 19.55–20.0 | 4.54–4.44 | 25–58 |
| 21.9–22.35 | 4.06–3.98 | 0–9 |
| 24.05–24.45 | 3.700–3.641 | 100 |
| 27.85–28.55 | 3.203–3.126 | 8–17 |
| 31.25–31.8 | 2.862–2.814 | 5–16 |
| 34.35–35.0 | 2.611–2.564 | 12–22 |
| 37.3–37.5 | 2.411–2.398 | 0–3 |
| 39.9–40.4 | 2.259–2.233 | 2–6 |
| 42.5–43.0 | 2.127–2.103 | 3–24 |
| 47.25–47.8 | 1.924–1.903 | 2–8 |
| 51.6–52.2 | 1.771–1.752 | 2–17 |

Preparation 8

(a) A reaction mixture was prepared by adding 1.09 grams of a reactive amorphous precipitated silica (91.4 wt.-% SiO$_2$, 8.6 wt.-% H$_2$O) to a solution of 14.50 grams of tetramethylammonium hydroxide pentahydrate (TMAOH.5 H$_2$O) in 20.0 grams of water, and mixed until homogeneous. To this mixture were added 6.12 grams of a hydrated aluminum oxide (a pseudo-boehmite phase, 74.2 wt.-% Al$_2$O$_3$, 25.8 wt.-% H$_2$O) and 9.55 grams of 85% orthophosphoric acid (H$_3$PO$_4$) and 6.21 grams of water and the mixture stirred until homogeneous. The composition of the final reaction mixture in molar oxide ratios was:

$$1.1Al_2O_3:1.0P_2O_5:1.0(TMA)_2O:0.4SiO_2:50.0H_2O$$

Part of the reaction mixture was placed in a stainless steel pressure vessel with an inert plastic liner and heated in an oven at 200° C. at autogenous pressure for 24 hours. The solid reaction product was recovered by filtering, washed with water, and dried in air at room temperature. The SAPO-20 product had an X-ray powder diffraction pattern characterized by the following data:

TABLE P

| 2θ | d | 100 × I/I₀ |
|---|---|---|
| 14.1 | 6.28 | 39 |
| 19.8 | 4.48 | 49 |
| 22.2 | 4.00 | 6 |
| 24.3 | 3.66 | 100 |
| 28.1 | 3.175 | 11 |
| 31.7 | 2.822 | 12 |
| 34.7 | 2.585 | 16 |
| 37.5 | 2.398 | 1 |
| 40.2 | 2.243 | 5 |
| 42.7 | 2.117 | 6 |
| 47.5 | 1.914 | 6 |
| 51.9 | 1.762 | 12 |

(b) Adsorption capacities were measured on this calcined (500° C. for one hour) product using a standard McBain-Bakr gravimetric adsorption apparatus. The following data were obtained on a sample activated at 350° C. in vacuum.

| | Kinetic Diameter, A | Pressure, Torr | Temp °C. | Wt. % Adsorbed |
|---|---|---|---|---|
| O$_2$ | 3.46 | 100 | −183 | 0 |
| O$_2$ | 3.46 | 750 | −183 | 0 |
| H$_2$O | 2.65 | 4.6 | 24 | 32.1 |
| H$_2$O | 2.65 | 20 | 24 | 39.8 |

The pore size of the calcined product is greater than 2.65 A as shown by adsorption of H$_2$O, kinetic diameter 2.65 A, and less than 3.46 A, as shown by no adsorption of O$_2$, kinetic diameter 3.46 A.

(c) The above product, after calcination and McBain adsorption studies, had an X-ray powder diffraction pattern characteristic of SAPO-20 (short scan).

| 2θ | d | 100 × I/I₀ |
|---|---|---|
| 14.0 | 6.33 | 100 |
| 19.8 | 4.48 | 38 |
| 22.2 | 4.00 | 8 |
| 24.3 | 3.663 | 95 |
| 28.2 | 3.164 | 23 |
| 31.5 | 2.840 | 18 |
| 34.6 | 2.592 | 20 |

(d) EDAX (energy dispersive analysis by X-ray) microprobe analysis performed in conjunction with SEM (scanning electron microscope) study, on clean crystals having a crystal morphology characteristic of SAPO-20 gives the following analysis, based on relative peak heights:

| | Area Scan | Average of Spot Probes | Range |
|---|---|---|---|
| Si | 0.42 | 0.40 | 0.36–0.43 |
| Al | 1.0 | 1.0 | 1.0 |
| P | 0.77 | 0.79 | 0.76–0.85 |

The species SAPO-34 as referred to herein is a silicoaluminophosphate material having a three-dimensional microporous crystal framework structure of PO$_2$$^+$, AlO$_2$$^-$ and SiO$_2$ tetrahedral unit, and whose essential empirical chemical composition in the as-synthesized form and on an anhydrous basis is:

$$mR: (Si_xAl_yP_z)O_2$$

wherein "R" represents at least one organic templating agent present in the intracrystalline pore system; "m" represents the moles of "R" present per mole of $(Si_xAl_yP_z)O_2$ and has a value of from 0.02 to 0.3, "x", "y" and "z" represent respectively, the mole fractions of silicon, aluminum and phosphorus present in the oxide moiety, said mole fractions being within the compositional area bounded by points A, B, C, D and E on the ternary diagram which is FIG. 1, or preferably within the area bounded by points a, b, c, d and e on the ternary diagram which is FIG. 2, said silicoaluminophosphate having a characteristic X-ray powder diffraction pattern which contains at least the d-spacings set forth below in Table XI.

TABLE XI

| 2θ | d | Relative Intensity |
|---|---|---|
| 9.45–9.65 | 9.36–9.17 | s–vs |
| 16.0–16.2 | 5.54–5.47 | w–m |
| 17.85–18.15 | 4.97–4.89 | w–s |
| 20.55–20.9 | 4.32–4.25 | m–vs |
| 24.95–25.4 | 3.57–3.51 | w–s |
| 30.5–30.7 | 2.931–2.912 | w–s |

All of the as-synthesized SAPO-34 compositions for which X-ray powder diffraction data have presently been obtained have patterns which are within the generalized pattern of Table XII, below.

TABLE XII

| $2\theta$ | d | $100 \times I/I_o$ |
|---|---|---|
| 9.45–9.65 | 9.36–9.17 | 81–100 |
| 12.8–13.05 | 6.92–6.78 | 8–20 |
| 13.95–14.2 | 6.35–6.24 | 8–23 |
| 16.0–16.2 | 5.54–5.47 | 25–54 |
| 17.85–18.15 | 4.97–4.89 | 11–76 |
| 19.0 | 4.67 | 0–2 |
| 20.55–20.9 | 4.32–4.25 | 44–100 |
| 22.05–22.5 | 4.03–3.95 | 0–5 |
| 23.0–23.15 | 3.87–3.84 | 2–10 |
| 24.95–25.4 | 3.57–3.51 | 12–87 |
| 25.8–26.0 | 3.45–3.43 | 14–26 |
| 27.5–27.7 | 3.243–3.220 | 1–4 |
| 28.05–28.4 | 3.181–3.143 | 1–12 |
| 29.2–29.6 | 3.058–3.018 | 3–9 |
| 30.5–30.7 | 2.931–2.912 | 19–75 |
| 31.05–31.4 | 2.880–2.849 | 15–28 |
| 32.2–32.4 | 2.780–2.763 | 1–5 |
| 33.4–33.85 | 2.683–2.648 | 0–6 |
| 34.35–34.65 | 2.611–2.589 | 4–15 |
| 36.0–36.5 | 2.495–2.462 | 2–11 |
| 38.8–38.9 | 2.321–2.315 | 0–2 |
| 39.6–39.7 | 2.276–2.270 | 2–4 |
| 43.1–43.5 | 2.099–2.080 | 3–6 |
| 47.4–47.7 | 1.918–1.907 | 2–6 |
| 48.8–49.2 | 1.866–1.852 | 4–7 |
| 49.9–50.45 | 1.828–1.809 | 0–2 |
| 50.65–51.3 | 1.802–1.781 | 1–8 |
| 53.0–53.25 | 1.728–1.720 | 2–7 |
| 54.25–54.7 | 1.691–1.678 | 0–4 |
| 55.7–55.9 | 1.650–1.645 | 2–5 |

Preparation 9

In the preparation of SAPO-34, a reaction mixture was formed by combining 28.8 grams of 85 wt.-% orthophosphoric acid ($H_3PO_4$) with a mixture of 17.2 grams of a hydrated aluminum oxide (a pseudo-boehmite phase, 74.2 wt.-% $Al_2O_3$, 25.8 wt.-% $H_2O$) in 18.4 grams of water. To this mixture was added 151.7 grams of an aqueous solution of 40.7 wt.-% tetraethylammonium hydroxide (TEAOH) and the mixture stirred until homogeneous. To 81.9 grams of this mixture was added a solution of 11.7 grams of sodium aluminate ($Al_2O_3$:1.2-1$Na_2O$:3.2$H_2O$) in 23.0 grams of water and 40.0 grams of an aqueous sol of 30 wt.-% $SiO_2$, and the mixture stirred until homogeneous. The composition of the final reaction mixture in molar oxide ratios was:

1.6(TEA)$_2$O:1.2Na$_2$O:4SiO$_2$:2Al$_2$O$_3$:P$_2$O$_5$:112H$_2$O

Part of the reaction mixture was sealed in a stainless steel pressure vessel having an inert plastic liner, and heated in an oven at 200° C. at autogenous pressure for 168 hours. The solid reaction product was recovered by filtration, washed with water, and dried in air at 110° C. The crystalline product was impure but the major phase, SAPO-34, had an X-ray powder diffraction pattern characterized by the following data:

TABLE Q

| $2\theta$ | d | $100 \times I/I_o$ |
|---|---|---|
| 9.6 | 9.21 | 100 |
| 13.0 | 6.81 | 17 |
| 14.05 | 6.30 | 23 |
| 16.1 | 5.50 | 33 |
| 17.85 | 4.97 | 75 |
| 19.0 | 4.67 | 2 |
| 20.7 | 4.29 | 99 |
| 22.05 | 4.03 | 4 |
| 23.1 | 3.85 | 10 |
| 24.95 | 3.57 | 76 |
| 26.0 | 3.43 | 19 |
| 27.7 | 3.220 | 3 |
| 28.15 | 3.170 | 12* |
| 29.4 | 3.038 | 4 |
| 30.7 | 2.912 | 67 |
| 31.05 | 2.880 | 28 |
| 32.4 | 2.763 | 2 |
| 33.4 | 2.683 | 6 |
| 34.55 | 2.596 | 14 |
| 36.0 | 2.495 | 11 |
| 39.7 | 2.270 | 4 |
| 43.4 | 2.085 | 3 |
| 47.6 | 1.910 | 6 |
| 48.8 | 1.866 | 7 |
| 49.2 | 1.852 | 5 |
| 50.65 | 1.802 | 8 |
| 53.2 | 1.722 | 6 |
| 54.25 | 1.691 | 4 |
| 55.9 | 1.645 | 4 |

*contains peak from an impurity.

By chemical analysis, the composition of the solid product was established to be 2.8 wt.-% C, 0.5 wt.-% N, 37.0 wt.-% $SiO_2$, 27.6 wt.-% $Al_2O_3$, 12.2 wt.-% $P_2O_5$, 7.4 wt.-% $Na_2O$, 15.9 wt.-% LOI, giving an overall product composition in molar oxide ratios of:

0.05(TEA)$_2$O:2.3SiO$_2$:0.4Na$_2$O:Al$_2$O$_3$:0.3P$_2$O$_5$:2.4H$_2$O

Preparation 10

(a) A reaction mixture was prepared by combining 81.7 grams of aluminum isopropoxide (Al(OC$_3$H$_7$)$_3$) with a solution of 46.1 grams of 85 wt.-% orthophosphoric acid in 104.9 grams of water, while stirring. To this mixture were added 12 grams of an aqueous sol of 30 wt.-% $SiO_2$ and 5 grams of water, and the mixture stirred until homogeneous. To this mixture was added 73.7 grams of an aqueous solution of 40 wt.-% tetraethylammonium hydroxide (TEAOH). One half by weight of this mixture was combined with 36.8 grams of 40% TEAOH, and the mixture stirred until homogeneous. The composition of the final reaction mixture in molar oxide ratios was:

(TEA)$_2$O:0.3SiO$_2$:Al$_2$O$_3$:P$_2$O$_5$:50.0H$_2$O

The reaction mixture was placed in a stainless steel pressure vessel lined with an inert plastic material (polytetrafluoroethylene) and heated in an oven at 200° C. at autogeneous pressure for 120 hours. The solid reaction product (SAPO-34) was recovered by centrifugation, washed with water, and dried in air at 100° C. By chemical analysis, the product was established to comprise 10.5 wt.-% C, 1.6 wt.-% N, 34.1 wt.-% Al$_2$O$_3$, 39.2 wt.-% P$_2$O$_5$, 6.8 wt.-% SiO$_2$ and 19.2 wt.-% LOI, giving a product composition in molar oxide ratios of:

0.17(TEA)$_2$O:0.33SiO$_2$:Al$_2$O$_3$:0.82P$_2$O$_5$0.40H$_2$O, which corresponds to the formula (anhydrous basis)

0.09(TEA).(Si$_{0.08}$Al$_{0.51}$P$_{0.41}$)O$_2$

The above product had an X-ray powder diffraction pattern essentially identical to that in Preparation 9.

(b) A portion of the solid crystalline SAPO-34 of part (a) was calcined in air at 550° C. for 2 hours. Adsorption capacities were measured on this calcined product using a standard McBain-Bakr gravimetric adsorption apparatus. The following data were obtained on a sample activated at 350° C.

| | Kinetic Diameter, A | Pressure, Torr | Temp., °C. | Wt. % Adsorbed |
|---|---|---|---|---|
| O$_2$ | 3.46 | 104 | −183 | 25.1 |
| O$_2$ | 3.46 | 746 | −183 | 36.6 |
| n-Hexane | 4.3 | 46 | 23.4 | 11.0 |
| H$_2$O | 2.65 | 4.6 | 23.0 | 30.1 |
| H$_2$O | 2.65 | 19.5 | 22.8 | 42.3 |

The pore size of the calcined product is greater than 4.3 A, as shown by adsorption of n-hexane, kinetic diameter of 4.3 A.

(c) The product after McBain adsorption studies had an X-ray powder diffraction pattern charcterized by the following data:

TABLE S

| 2θ | d | 100 × I/I$_o$ |
|---|---|---|
| 9.45 | 9.36 | 100 |
| 12.95 | 6.84 | 25 |
| 14.0 | 6.33 | 5 |
| 16.1 | 5.50 | 27 |
| 16.9 | 5.25 | 3 |
| 17.7 | 5.01 | 9 |
| 19.05 | 4.66 | 3 |
| 20.75 | 4.28 | 55 |
| 21.25 | 4.18 | 1 |
| 22.0 | 4.04 | 3 |
| 22.55 | 3.94 | 2 |
| 23.15 | 3.84 | 4 |
| 24.8 | 3.59 | 21 |
| 25.05 | 3.555 | 11 |
| 27.8 | 3.209 | } 4 |
| 28.1 (sh) | 3.175 | |
| 29.6 | 3.018 | 3 |
| 30.8 | 2.903 | 26 |
| 31.6 | 2.831 | 2 |
| 32.3 | 2.772 | 2 |
| 33.3 | 2.691 | 2 |
| 34.7 | 2.585 | 4 |
| 35.85 | 2.505 | 4 |
| 38.6 | 2.332 | 1 |
| 39.85 | 2.262 | 2 |
| 42.7 | 2.118 | 2 |
| 43.5 | 2.080 | 2 |
| 47.05 | 1.932 | 1 |
| 47.9 | 1.899 | 2 |
| 48.8 | 1.866 | 4 |
| 50.5 | 1.807 | 3 |
| 51.9 | 1.762 | 1 |
| 53.4 | 1.716 | 2 |
| 54.15 | 1.694 | 2 |
| 54.6 | 1.681 | 1 |

Preparation 11

SAPO-34 was crystallized from a reaction system containing both sodium and TEA ions prepared by combining 66.4 grams of aluminum isopropoxide with a solution of 28.8 grams of 85 wt.-% orthophosphoric acid in 70.1 grams of H$_2$O. To this mixture was added a mixture of 15.0 grams of an aqueous silica sol (30 wt.-% SiO$_2$) and a solution of 3.0 grams of NaOH in 10.0 grams H$_2$O. Thereafter 46.0 grams of an aqueous solution of 40 wt.-% tetraethylammonium hydroxide was added and the mixture stirred until homogeneous. The composition of the final mixture was:

0.5(TEA)$_2$O:0.3Na$_2$O:1.3Al$_2$O$_3$:0.6SiO$_2$:P$_2$O$_5$:60H$_2$O

After crystallization in a sealed reactor at 200° C. for 187 hours, the SAPO-34 product (identified by X-ray analysis) had a chemical composition: 4.5 wt.-% C, 37.7 wt.-% Al$_2$O$_3$, 22.9 wt.-% LOI, 29.5 wt.-% P$_2$O$_5$, 4.9 wt.-% Na$_2$O and 4.5 wt.-% SiO$_2$.

SAPO-35

The species SAPO-35 as referred to herein is a silicoaluminophosphate material having a three-dimensional microporous crystal framework structure of PO$_2^+$, AlO$_2^-$ and SiO$_2$ tetrahedral units, and whose essential empirical chemical composition on an anhydrous basis is:

mR: (Si$_x$Al$_y$P$_z$)O$_2$ wherein "R" represents at least one organic templating agent present in the intracrystalline pore system; "m" represents the moles of "R" present per mole of (Si$_x$Al$_y$P$_z$)O$_2$ and has a value of from zero to 0.3, "x", "y" and "z" represent respectively, the mole fractions of silicon, aluminum and phosphorus present in the oxide moiety, said mole fractions being within the compositional area bounded by points A, B, C, D and E on the ternary diagram which is FIG. 1, or preferably within the area bounded by points a, b, c, d and e on the ternary diagram which is FIG. 2, said silicoaluminophosphate having a characteristic X-ray powder diffraction pattern which contains at least the d-spacings set forth below in Table XIII. In the form as synthesized in accordance with the process of this invention, "m" has a value of from 0.02 to 0.3.

TABLE XIII

| 2θ | d | Relative Intensity |
|---|---|---|
| 10.9–11.05 | 8.12–8.01 | m |
| 17.2–17.4 | 5.16–5.10 | } s |
| 17.4–17.7 (sh) | 5.10–5.01 | |
| 21.0–21.25 | 4.23–4.18 | m |
| 21.8–22.0 | 4.08–4.04 | vs |
| 32.0–32.15 | 2.797–2.784 | m |

All of the as-synthesized SAPO-35 compositions for which X-ray powder diffraction data have presently been obtained have patterns which are within the generalized pattern of Table XIV, below.

TABLE XIV

| 2θ | d | 100 × I/I$_o$ |
|---|---|---|
| 8.5–8.7 | 10.4–10.1 | 13–18 |
| 10.9–11.05 | 8.12–8.01 | 38–48 |
| 11.6–11.9 | 7.63–7.44 | 1–3 |
| 13.2–13.4 | 6.71–6.61 | 23–24 |
| 15.75–16.0 | 5.62–5.54 | 7–12 |
| 17.2–17.4 | 5.16–5.10 | } 66–83 |
| 17.4–17.7 (sh) | 5.10–5.01 | |
| 17.6–17.9 | 5.04–4.96 | 9–18 |
| 21.0–21.25 | 4.23–4.18 | 47–56 |
| 21.8–22.0 | 4.08–4.04 | 100 |
| 23.0–23.3 | 3.87–3.82 | 14–18 |
| 23.55–23.75 | 3.78–3.75 | 6 |
| 24.9–25.2 | 3.58–3.53 | 3–6 |
| 25.85–26.0 | 3.446–3.427 | 0–2 |
| 26.7–26.9 | 3.339–3.314 | 16–19 |
| 28.4–28.55 | 3.143–3.126 | 22–26 |
| 28.65–28.85 | 3.116–3.095 | 13–20 |
| 29.0–29.1 | 3.079–3.069 | 4–6 |
| 32.0–32.15 | 2.797–2.784 | 33–47 |
| 34.55–34.7 | 2.596–2.585 | 6–9 |
| 35.6–35.8 | 2.522–2.508 | 3–4 |
| 37.7–37.8 | 2.386–2.380 | 2–3 |
| 39.2–39.3 | 2.298–2.292 | 2 |
| 40.7–40.8 | 2.217–2.212 | 0–2 |
| 41.95–42.1 | 2.154–2.146 | 3–5 |

TABLE XIV-continued

| 2θ | d | 100 × I/I₀ |
|---|---|---|
| 42.4-42.55 | 2.132-2.125 | 2-4 |
| 42.95-43.2 | 2.106-2.094 | 2-4 |
| 44.4-44.5 | 2.040-2.036 | 1-2 |
| 48.4-48.55 | 1.881-1.875 | 7-8 |
| 49.3-49.45 | 1.848-1.843 | 6-8 |
| 51.4-51.5 | 1.778-1.774 | 5-8 |
| 55.2-55.25 | 1.664-1.663 | 4-7 |

Preparation 12

(a) A reaction mixture was prepared by combining 132 grams of water with 132.8 grams of aluminum isopropoxide (Al(OC₃H₇)₃) and then adding 30.1 grams of an aqueous sol containing 30 wt.-% SiO₂ and 45 grams of water. To this mixture was added 57.7 grams of 85 wt.-% orthophosphoric acid (H₃PO₄) and the mixture stirred until homogeneous. To this mixture was added a solution of 27.8 grams of quinuclidine, C₇H₁₃N, (Q) in 50 grams of water, and the mixture stirred until homogeneous. The composition of the final reaction mixture in molar oxide ratios was:

1.0Q:0.6SiO₂:1.3Al₂O₃:P₂O₅:60H₂O

Part of the reaction mixture was placed in a stainless steel pressure vessel lined with polytetrafluoroethylene and heated in an oven at 150° C. at autogenous pressure for 48 hours. The solid reaction product was recovered by centrifugation, washed in water, and dried in air at 100° C. The above product was impure but the major phase had an X-ray powder diffraction pattern essentially identical to that in Table T.

TABLE T

| 2θ | d | 100 × I/I₀ |
|---|---|---|
| 8.7 | 10.1 | 18 |
| 11.05 | 8.01 | 47 |
| 11.9 | 7.44 | 2 |
| 13.4 | 6.61 | 23 |
| 16.0 | 5.54 | 12 |
| 17.4 | 5.10 | |
| | | 83 |
| 17.7 (sh) | 5.01 | |
| 17.9 | 4.96 | 14 |
| 21.25 | 4.18 | 55 |
| 22.0 | 4.04 | 100 |
| 22.8 | 3.90 | 5 |
| 23.3 | 3.82 | 18 |
| 23.7 | 3.75 | 6 |
| 25.2 | 3.53 | 5 |
| 26.0 | 3.427 | 1 |
| 26.9 | 3.314 | 18 |
| 28.55 | 3.126 | 26 |
| 28.65 | 3.116 | 13 |
| 29.1 | 3.069 | 6 |
| 32.15 | 2.784 | 40 |
| 34.65 | 2.589 | 9 |
| 35.7 | 2.515 | 3 |
| 37.8 | 2.380 | 2 |
| 39.3 | 2.292 | 2 |
| 40.8 | 2.212 | 2 |
| 42.1 | 2.146 | 4 |
| 42.4 | 2.132 | 4 |
| 43.15 | 2.096 | 4 |
| 44.4 | 2.040 | 2 |
| 48.5 | 1.877 | 7 |
| 49.4 | 1.845 | 6 |
| 51.5 | 1.774 | 7 |
| 55.2 | 1.664 | 7 |

(b) A portion of the solid crystalline product was calcined in air at about 600° C. for 2 hours. The whiter portion of the calcined product had an X-ray powder pattern characterized by the following data:

TABLE U

| 2θ | d | 100 × I/I₀ |
|---|---|---|
| 6.8 | 13.0 | 2 |
| 8.2 | 10.78 | 2 |
| 8.7 | 10.16 | 14 |
| 11.0 | 8.04 | 100 |
| 11.4 | 7.76 | 17 |
| 13.55 | 6.53 | 89 |
| 16.1 | 5.50 | 4 |
| 17.4 | 5.10 | 24 |
| 18.7 | 4.75 | 3 |
| 21.0 | 4.23 | 29 |
| 22.2 | 4.00 | 63 |
| 23.0 | 3.87 | 4 |
| 23.6 | 3.77 | 15 |
| 25.05 | 3.555 | 13 |
| 26.0 | 3.427 | 9 |
| 27.3 | 3.267 | 20 |
| 28.6 | 3.121 | 42 |
| 29.5 | 3.028 | 10 |
| 30.6 | 2.921 | 2 |
| 31.75 | 2818 | 6 |
| 32.4 sh | 2.763 | 32 |
| 32.6 | 2.747 | |
| 34.6 | 2.592 | 7 |
| 35.4 | 2.536 | 4 |
| 36.3 | 2.475 | 2 |
| 47.9 | 1.899 | 2 |
| 51.7 | 1.768 | 3 |

(c) Adsorption capacities were measured on this calcined product using a standard McBain-Bakr gravimetric adsorption apparatus. The following data were obtained on a sample activated at 350° C.:

| | Kinetic Diameter, A | Pressure, Torr | Temp., °C. | Wt. % Adsorbed |
|---|---|---|---|---|
| O₂ | 3.46 | 98 | -183 | 15.3 |
| O₂ | 3.46 | 746 | -183 | 30.3 |
| isobutane | 5.0 | 101 | 25 | 0.7 |
| n-hexane | 4.3 | 48 | 24 | 10.2 |
| H₂O | 2.65 | 4.6 | 22 | 22.2 |
| H₂O | 2.65 | 19 | 24 | 47.7 |

The pore size of the calcined product is >4.3 A and <5.0 A as shown by adsorption of n-hexane, kinetic diameter of 4.3 A, and negligible adsorption of isobutane, kinetic diameter of 5.0 A.

SAPO-37

Figure 2:
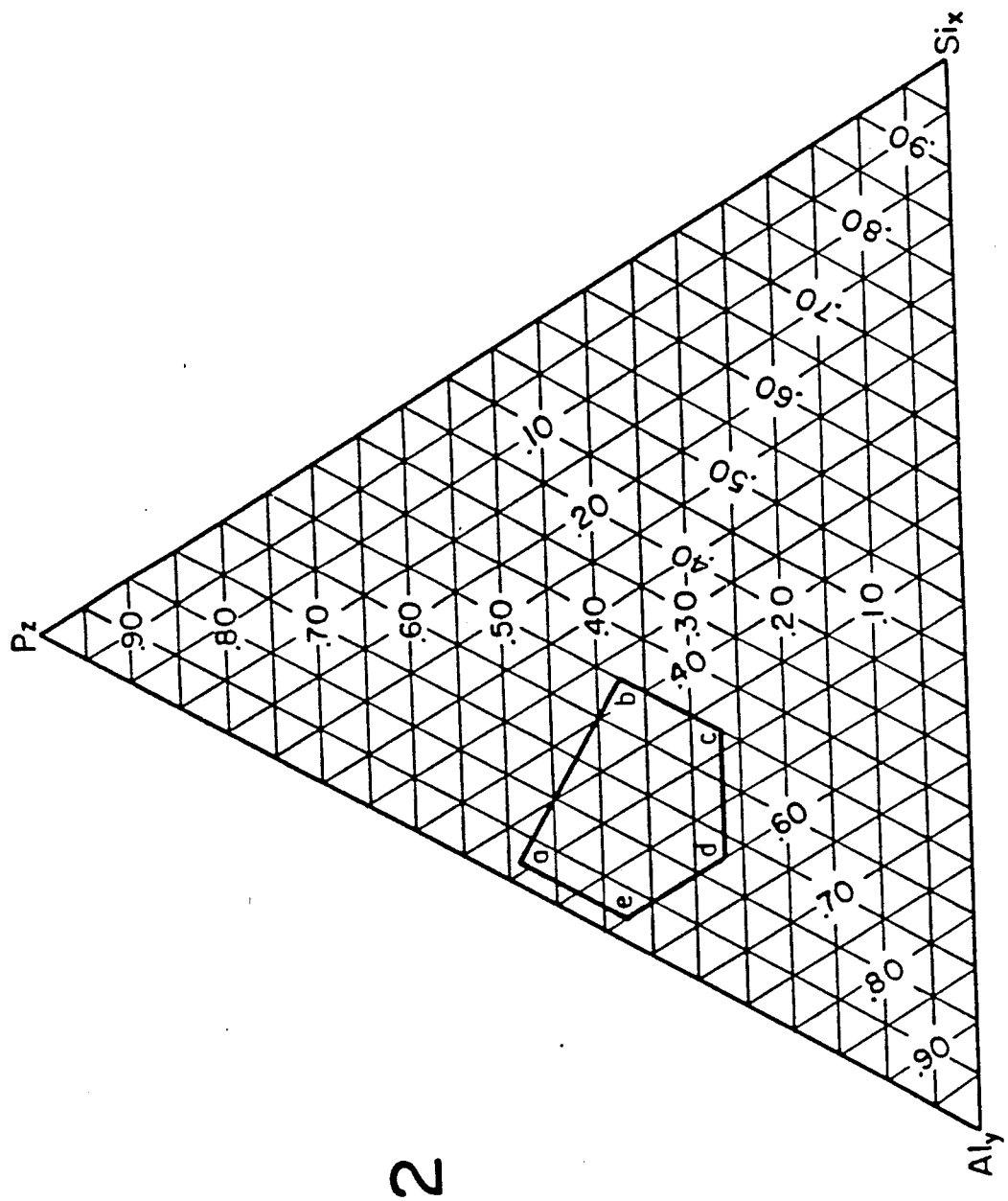
FIG. 2 is a ternary diagram showing the preferred compositional parameters of the silicoaluminophosphates useful in the process of this invention in terms of mole fractions of silicon, aluminum and phosphorus.
Figure 2:
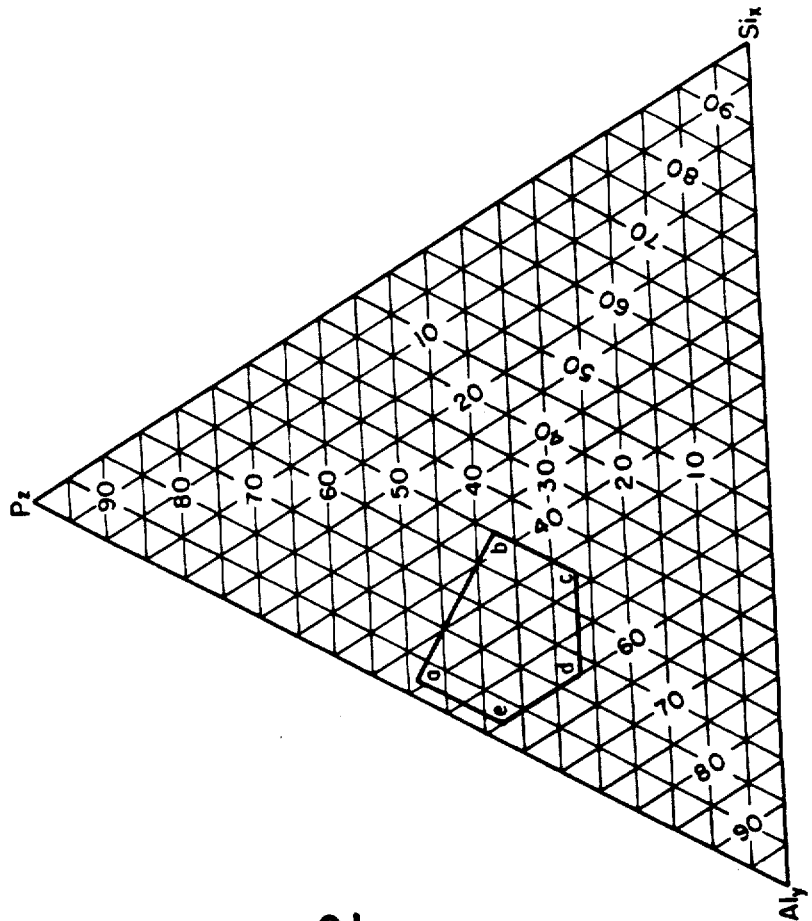

The species SAPO-37 as referred to herein is a silicoaluminophosphate having a microporous crystalline framework structure and whose essential empirical chemical composition in the as-synthesized form and on anhydrous basis is:

mR:(Si$_x$Al$_y$P$_z$)O$_2$ wherein R represents at least one organic templating agent present in the intracrystalline pore system, "m" has a value of from 0.02 to 0.3, "x", "y" and "z" represent, respectively, the mole fraction of silicon, aluminum and phosphorus present in the oxide moiety, the value of x, y and z being within the compositional area bounded by points A, B, C, D and E on the ternary diagram which is FIG. 1, or preferably within the area bounded by points a, b, c, d and e on the ternary diagram which is FIG. 2, said silicoaluminophosphate having a characteristic X-ray powder diffraction pattern which contains at least the d-spacings set forth below in Table XV:

TABLE XV

| $2\theta$ | d | Relative Intensity |
|---|---|---|
| 6.1–6.3 | 14.49–14.03 | vs |
| 15.5–15.7 | 5.72–5.64 | w-m |
| 18.5–18.8 | 4.80–4.72 | w-m |
| 23.5–23.7 | 3.79–3.75 | w-m |
| 26.9–27.1 | 3.31–3.29 | w-m |

All of the synthesized SAPO-37 compositions for which X-ray powder diffraction data have presently been obtained have patterns which are within the generalized pattern of Table XVI, below.

TABLE XVI

| $2\theta$ | d | $100 \times I/I_o$ |
|---|---|---|
| 6.1–6.3 | 14.49–14.03 | 100 |
| 10.1–10.3 | 8.76–8.59 | 22–30 |
| 11.8–12.0 | 7.50–7.37 | 4–10 |
| 15.5–15.7 | 5.72–5.64 | 30–60 |
| 18.5–18.8 | 4.80–4.72 | 20–50 |
| 20.2–20.4 | 4.40–4.35 | 12–26 |
| 21.0–21.2 | 4.23–4.19 | 4–10 |
| 22.7–22.9 | 3.92–3.88 | 8–21 |
| 23.5–23.7 | 3.79–3.75 | 24–59 |
| 24.6–24.9 | 3.62–3.58 | 1–3 |
| 25.6–25.8 | 3.48–3.45 | 5–11 |
| 26.9–27.1 | 3.31–3.29 | 14–42 |
| 27.6–27.9 | 3.232–3.198 | 2–4 |
| 29.4–29.7 | 3.038–3.008 | 2–11 |
| 30.6–30.8 | 2.921–2.903 | 5–18 |
| 31.2–31.5 | 2.867–2.840 | 12–32 |
| 32.2–32.5 | 2.780–2.755 | 3–11 |
| 33.0–33.2 | 2.714–2.698 | 1–3 |
| 33.9–34.2 | 2.644–2.622 | 4–14 |
| 34.3–34.5 | 2.614–2.600 | 2–6 |
| 37.7–38.0 | 2.386–2.368 | 3–9 |
| 40.4–40.7 | 2.232–2.217 | 1–5 |
| 41.2–41.5 | 2.191–2.176 | 1–7 |
| 43.1–43.3 | 2.099–2.089 | 1–7 |
| 43.9–44.1 | 2.062–2.053 | 2–8 |

Preparation 13

(a) SAPO-37 was found to be suitably templated by a mixture of tetra-n-propylammonium ions and tetramethylammonium ions in a reaction mixture formed by combining 27.7 grams of 85 wt.-% orthophosphoric acid ($H_3PO_4$) and 30.5 grams of water, to which was added 16.6 grams of hydrated aluminum oxide (a pseudo-boehmite phase, 74.2 wt.-% $Al_2O_3$, 25.8 wt.-% $H_2O$), and stirred until homogeneous. To this mixture was added a dispersion of 3.1 grams of a fumed silica (9.28 wt.-% $SiO_2$, 7.2 wt.-% $H_2O$) and 1.1 gram of tetramethylammonium hydroxide pentahydrate (TMAOH 5.$H_2O$) in 115.98 grams of an aqueous solution of 40 wt.-% tetra-n-propylammonium hydroxide (TPAOH) and the mixture stirred until homogeneous. The composition of the final reaction mixture in molar oxide ratios was:

$Al_2O_3:P_2O_5:0.4SiO_2:(TPA)_2O:0.025(TMA)_2O:50-H_2O$

A portion of the reaction mixture was placed in a stainless steel pressure vessel lined with polytetrafluoroethylene and heated in an oven at 200° C. at autogenous pressure for 24 hours. The solid reaction product was recovered by centrifuging and washing with water, and dried in air at 100° C. The above product had an X-ray powder diffraction pattern characterized by the following data:

TABLE W

| $2\theta$ | d | $100 \times I/I_o$ |
|---|---|---|
| 6.2 | 14.25 | 100 |
| 10.1 | 8.74 | 22 |
| 11.9 | 7.44 | 5 |
| 15.6 | 5.68 | 42 |
| 18.5 | 4.80 | 34 |
| 20.2 | 4.40 | 16 |
| 21.2 | 4.19 | 4 |
| 22.7 | 3.92 | 11 |
| 23.5 | 3.79 | 39 |
| 24.8 | 3.59 | 1 |
| 25.7 | 3.47 | 6 |
| 26.9 | 3.314 | 27 |
| 27.6 | 3.232 | 2 |
| 29.4 | 3.038 | 7 |
| 30.6 | 2.921 | 9 |
| 31.2 | 2.867 | 18 |
| 32.2 | 2.780 | 5 |
| 33.0 | 2.714 | 2 |
| 33.9 | 2.644 | 7 |
| 34.4 | 2.607 | 3 |
| 37.8 | 2.380 | 6 |
| 40.4 | 2.233 | 2 |
| 41.2 | 2.191 | 2 |
| 43.1 | 2.099 | 1 |
| 43.9 | 2.062 | 3 |

The chemical composition of the SAPO-37 product was determined to be 31.8 wt.-% $Al_2O_3$, 31.4 wt.-% $P_2O_5$, 9.2 wt.-% $SiO_2$, 14.2 wt.-% C, 1.8 wt.-% N and 26.1 wt.-% LOI, corresponding to a product composition in molar oxide ratios of:

$1.0Al_2O_3:0.71P_2O_5:0.49SiO_2:0.13(TPA)_2O:0.07(TMA)_2O:0.89H_2O$, and thus had the formula (anhydrous basis):

$0.10(TPA+TMA):(Si_{0.125}Al_{0.51}P_{0.365})O_2$ (b) A portion of the solid crystalline product of part (a) was calculated in air at about 600° C. for 1 hour. The calcined product had an X-ray powder diffraction pattern characterized by the data shown in the following table:

TABLE Y

| $2\theta$ | d | $100 \times I/I_o$ |
|---|---|---|
| 6.2 | 14.25 | 100 |
| 10.3 | 8.59 | 19 |
| 12.1 | 7.37 | 11 |
| 15.9 | 5.57 | 20 |
| 18.6 | 4.77 | 7 |
| 20.4 | 4.35 | 9 |
| 21.5 | 4.13 | 1 |
| 22.9 | 3.88 | 3 |
| 23.8 | 3.74 | 13 |
| 25.0 | 3.56 | 1 |
| 25.8 | 3.45 | 1 |
| 27.0 | 3.30 | 7 |
| 27.7 | 3.22 | 1 |
| 29.5 | 3.03 | 2 |
| 30.7 | 2.92 | 4 |
| 31.4 | 2.85 | 7 |
| 32.4 | 2.76 | 2 |
| 33.0 | 2.71 | 1 |
| 34.0 | 2.63 | 3 |
| 34.6 | 2.59 | 1 |
| 37.9 | 2.37 | 2 |
| 40.5 | 2.23 | 1 |
| 41.2 | 2.19 | 1 |
| 43.1 | 2.10 | 1 |

TABLE Y-continued

| $2\theta$ | d | $100 \times I/I_o$ |
|---|---|---|
| 44.0 | 2.06 | 1 |

(c) Adsorption capacities were measured on this calcined product using a standard McBain-Bakr gravimetric adsorption apparatus. The following data were obtained on a sample activated at 350° C. in vacuum.

| | Kinetic Diameter, A | Pressure, Torr | Temp., °C. | Wt. % Adsorbed |
|---|---|---|---|---|
| $O_2$ | 3.46 | 100 | −183 | 35.0 |
| $O_2$ | 3.46 | 750 | −183 | 42.9 |
| Cyclohexane | 6.0 | 60 | 24 | 23.2 |
| Neopentane | 6.2 | 743 | 24 | 14.8 |
| $H_2O$ | 2.65 | 4.6 | 24 | 35.3 |

The pore size of the calcined product is greater than 6.2 A, as shown by adsorption of neopentane, kinetic diameter of 6.2 A.

(d) EDAX (energy dispersive analysis by X-ray) microprobe analysis, performed in conjunction with SEM (scanning electron microscope) study, on clean crystals having a crystal morphology characteristic of SAPO-37 gives the following analysis based on relative peak heights:

Si: 1
Al: 3
P: 2

(e) Mixtures of tetramethylammonium hydroxide with tri-n-propylamine and with tetra-n-butylammonium hydroxide were also found to facilitate the formation of SAPO-37.

SAPO-40

The species SAPO-40 as referred to herein is a silicoaluminophoshate material having a three-dimensional microporous crystal framework structure of $PO_2{}^+$, $AlO_2{}^-$ and $SiO_2$ tetrahedral units, and whose essential empirical chemical composition on an anhydrous basis is:

$$mR:(Si_xAl_yP_x)O_2$$

wherein "R" represents at least one organic templating agent present in the intracrystalline pore system; "m" represents the moles of "R" present per mole of $(Si_xAl_yP_z)O_2$ and has a value of from zero to 0.3, "x", "y" and "z" represent respectively, the mole fractions of silicon, aluminum and phosphorus present in the oxide moiety, said mole fractions being within the composition area bounded by points A, B, C, D and E on the ternary diagram which is FIG. 1, or preferably within the area bounded by points a, b, c, d and e on the ternary diagram which is FIG. 2, said silicoaluminophosphate having a characteristic X-ray powder diffraction pattern which contains at least the d-spacings set forth below in Table XVII. In the form as synthesized in accordance with the process of this invention, "m" has a value of from 0.02 to 0.3.

TABLE XVII

| | SAPO-40 | |
|---|---|---|
| $2\theta$ | d | Relative Intensity |
| 7.5–7.7 | 11.79–11.48 | VW–M |

TABLE XVII-continued

| | SAPO-40 | |
|---|---|---|
| $2\theta$ | d | Relative Intensity |
| 8.0–8.1 | 11.05–10.94 | S–VS |
| 12.4–12.5 | 7.14–7.08 | W–VS |
| 13.6–13.8 | 6.51–6.42 | M–S |
| 14.0–14.1 | 6.33–6.28 | W–M |
| 27.8–28.0 | 3.209–3.18 | W–M |

All of the as-synthesized SAPO-40 compositions for which X-ray powder diffraction data have presently been obtained have patterns which are within the generalized pattern of Table XVIII, below.

TABLE XVIII

| $2\theta$ | d | $100 \times I/I_o$ |
|---|---|---|
| 7.5–7.71 | 11.79–11.48 | 6–51 |
| 8.0–8.11 | 11.05–10.94 | 85–100 |
| 12.4–12.5 | 7.14–7.08 | 15–100 |
| 13.6–13.8 | 6.51–6.42 | 43–62 |
| 14.0–14.1 | 6.33–6.28 | 12–36 |
| 16.1–16.3 | 5.50–5.44 | 1–2 |
| 17.3–17.7 | 5.13–5.01 | 6–17 |
| 18.5–18.6 | 4.80–4.77 | 14–30 |
| 19.7–29.0 | 4.51–4.44 | 6–22 |
| 20.3–20.5 | 4.37–4.33 | 12–19 |
| 21.3–21.5 | 4.17–4.13 | 10–19 |
| 21.6–21.9 | 4.11–4.06 | 6–22 |
| 22.9—23.2 | 3.88–3.83 | 4–9 |
| 23.7–23.8 | 3.75–3.74 | 19–30 |
| 24.0–24.3 | 3.71–3.66 | 0–5 |
| 24.6–24.7 | 3.62–3.60 | 1–17 |
| 27.3–27.5 | 3.267–3.24 | 22–29 |
| 27.8–28.0 | 3.209–3.18 | 15–33 |
| 28.0–28.2 | 3.187–3.164 | 0–4 |
| 28.5–28.7 | 3.132–3.110 | 0–2 |
| 29.2–29.3 | 3.058–3.048 | 0–9 |
| 30.3–30.4 | 2.950–2.940 | 0–3 |
| 30.6–30.7 | 2.921–2.912 | 0–2 |
| 31.0–31.2 | 2.885–2.867 | 0–3 |
| 31.7–31.9 | 2.823–2.805 | 4–5 |
| 32.3–32.5 | 2.772–2.775 | 3–5 |
| 33.2–33.4 | 2.698–2.683 | 1–2 |
| 33.7–33.8 | 2.660–2.652 | 2–3 |
| 35.0–35.2 | 2.564–2.550 | 2–3 |
| 35.8–35.9 | 2.508–2.501 | 2–3 |

Preparation 14

(a) SAPO-40 was produced by crystallizing at 200° C. for 96 hours under autogenous pressure a reaction mixture containing both sodium hydroxide and TPAOH in addition to phosphoric acid, a hydrated aluminum oxide, water and a fumed silica in proportions such that the reaction mixture had the composition:

$$Al_2O_3:P_2O_5:0.4SiO_2:(TPA)_2O:0.01Na_2O:50H_2O$$

A portion of the recovered solids was analyzed with X-radiation to produce a powder diffraction pattern characterized by the following data (peaks resulting solely from a minor SAPO-5 impurity have been omitted):

TABLE AA

| $2\theta$ | d | $100 \times I/I_o$ |
|---|---|---|
| 7.60 | 11.63 | 18* |
| 8.03 | 11.01 | 100 |
| 12.43 | 7.12 | 18 |
| 13.68 | 6.47 | 43 |
| 14.02 | 6.32 | 12 |
| 16.12 | 5.50 | 1 |
| 17.36 | 5.11 | 7 |
| 18.50 | 4.80 | 14 |
| 19.72 | 4.50 | 6 |

TABLE AA-continued

| 2θ | d | 100 × I/I₀ |
|---|---|---|
| 20.39 | 4.36 | 13 |
| 21.40 | 4.15 | 10 |
| 21.68 | 4.10 | 6 |
| 22.93 | 3.88 | 4 |
| 23.74 | 3.75 | 19 |
| 24.21 | 3.68 | 5 |
| 24.62 | 3.61 | 1 |
| 27.32 | 3.264 | 22 |
| 27.84 | 3.204 | 15 |
| 28.10 | 3.176 | 4 |
| 28.59 | 3.123 | 1 |
| 30.34 | 2.946 | 3 |
| 30.61 | 2.920 | 2 |
| 31.07 | 2.878 | 3 |
| 31.76 | 2.817 | 4 |
| 32.33 | 2.769 | 3 |
| 33.28 | 2.692 | 2 |
| 33.77 | 2.654 | 2 |
| 35.07 | 2.559 | 2 |
| 35.82 | 2.507 | 3 |

*Contains peak from impurity

Chemical analysis indicated the product contained 8.9 wt.-% C, 1.0 wt.-% N, 34.4 wt.-% $Al_2O_3$, 40.4 wt.-% $P_2O_5$, 6.9 wt.-% $SiO_2$, 0.7 wt.-% $Na_2O$, 17.5 wt.-% LOI, giving a product composition in molar oxide ratios of:

$$0.092(TPA)_2O:0.034Na_2O:1.00Al_2O_3:0.85P_2O_5:0.34SiO_2:0.81H_2O,$$

and a formula (anhydrous basis)

$$[0.045(TPA),0.017Na]:(Si_{0.085}Al_{0.495}P_{0.42})O_2$$

(b) A portion of the product of part (a) supra was calcined in air at 700° C. for 1 hour. The X-ray pattern of the calcined material was characterized by the following data after subtraction of peaks contributed by identified impurities:

TABLE BB

| 2θ | d | 100 × I/I₀ |
|---|---|---|
| 7.60 | 11.63 | 78 |
| 7.95 | 11.19 | 100 |
| 12.55 | 7.08 | 14 |
| 13.60 | 6.51 | 13 |
| 14.20 | 6.24 | 13 |
| 16.00 | 5.54 | 3 |
| 17.40 | 5.10 | 9 |
| 18.60 | 4.77 | 15 |
| 20.40 | 4.35 | 7 |
| 21.65 | 4.11 | 4 |
| 22.75 | 3.92 | 3 |
| 23.70 | 3.75 | 3 |
| 27.15 | 3.290 | 15 |
| 28.00 | 3.186 | 12 |
| 30.65 | 2.921 | 3 |
| 31.70 | 2.822 | 3 |
| 32.40 | 2.763 | 2 |

(c) Adsorption capacities were measured on this calcined product using a standard McBain-Bakr gravimetric adsorption apparatus. The following data were obtained on a sample activated at 350° C. in vacuum.

| | Kinetic Diameter, A | Pressure, Torr | Temp., °C. | Wt % Adsorbed |
|---|---|---|---|---|
| O₂ | 3.46 | 100 | −183 | 21.8 |
| O₂ | 3.46 | 750 | −183 | 24.4 |
| Cyclohexane | 6.0 | 60 | 24 | 8.0 |
| Neopentane | 6.2 | 743 | 24 | 5.1 |
| H₂O | 2.65 | 4.6 | 24 | 22.7 |
| H₂O | 2.65 | 20 | 24 | 31.5 |
| Isobutane | 5.0 | 697 | 24 | 7.0 |
| SF₆ | 5.5 | 400 | 24 | 11.6 |

The pore size of the calcined product appears to be greater than 6.2 A, as shown by adsorption of neopentane, kinetic diameter 6.2 A. It should be noted, however, that the sample contained substantial amounts of SAPO-5, which adsorbs molecules as large as neopentane.

(d) EDAX (energy dispersive analysis by X-ray) microprobe analysis, performed in conjunction with SEM (scanning electron microscope) study, on clean crystals having a crystal morphology characteristic of SAPO-40 gives the following analysis based on relative peak heights:

Si: 0.14
Al: 1.0
P: 0.95

SAPO-42

The species SAPO-42 as referred to herein is a silicoaluminophosphate having a microporous crystalline framework structure and whose empirical chemical composition in the as-synthesized form and an anhydrous basis:

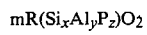

$$mR(Si_xAl_yP_z)O_2$$

wherein R represents at least one organic templating agent present in the intracrystalline pore system, "m" has a value of from 0.02 to 0.3, "x", "y" and "z" represent, respectively, the mole fraction of silicon, aluminum and phosphorus present in the oxide moiety, the value of x, y and z being within the compositional area bounded by points A, B, C, D and E on the ternary diagram which is FIG. 1, or preferably within the area bounded by points a, b, c, d and e on the ternary diagram which is FIG. 2., said silicoaluminophosphate having a characteristic X-ray powder diffraction pattern which contains at least the d-spacings set forth below in Table XIX:

TABLE XIX

| 2θ | d | Relative Intensity |
|---|---|---|
| 7.15–7.4 | 12.36–11.95 | M–VS |
| 12.5–12.7 | 7.08–6.97 | M–S |
| 21.75–21.9 | 4.086–4.058 | M–S |
| 24.1–24.25 | 3.69–3.67 | VS |
| 27.25–27.4 | 3.273–3.255 | S |
| 30.05–30.25 | 2.974–2.955 | M–S |

All of the as-synthesized SAPO-42 compositions for which X-ray powder diffraction data have presently been obtained have patterns which are within the generalized pattern of Table XX, below:

TABLE XX

| 2θ | d | 100 × I/I₀ |
|---|---|---|
| 6.75–6.85 | 13.09–12.90 | sh–13 |
| 7.15–7.4 | 12.36–11.95 | 51–100 |
| 10.2–10.4 | 8.67–8.51 | 42–65 |
| 12.5–12.7 | 7.08–6.97 | 48–74 |
| 13.65–13.9 | 6.49–6.37 | 5–10 |

TABLE XX-continued

| 2θ | d | 100 × I/I₀ |
|---|---|---|
| 16.2–16.35 | 5.47–5.42 | 31–37 |
| 17.7–17.9 | 5.01–4.96 | 11–17 |
| 20.5 | 4.33 | 0–3 |
| 21.5–21.6 | 4.13–4.11 | sh–12 |
| 21.75–21.9 | 4.086–4.058 | 53–72 |
| 22.95–23.1 | 3.875–3.850 | 13–20 |
| 24.1–24.25 | 3.693–3.670 | 91–100 |
| 26.2–26.4 | 3.401–3.376 | 19–29 |
| 27.25–27.4 | 3.273–3.255 | 73–87 |
| 27.7 | 3.220 | 0–6 |
| 30.05–30.25 | 2.974–2.955 | 64–80 |
| 31.0–31.1 | 2.885–2.876 | 10–16 |
| 32.65–32.9 | 2.743–2.722 | 16–21 |
| 33.55–33.7 | 2.671–2.660 | 6–10 |
| 34.35–34.45 | 2.612–2.603 | 32–39 |
| 35.9–36.05 | 2.501–2.491 | 13–19 |
| 36.75–36.9 | 2.445–4.436 | 3–8 |
| 38.15–38.25 | 2.359–2.347 | 5–8 |
| 40.35–40.5 | 2.235–2.227 | 7–11 |
| 41.7–41.95 | 2.166–2.154 | 8–13 |
| 42.35–42.55 | 2.134–2.125 | 5–13 |
| 43.15–43.4 | 2.096–2.085 | 0–3 |
| 43.8–43.85 | 2.067–2.065 | 0–2 |
| 44.45–44.55 | 2.038–2.034 | 6–9 |
| 47.55–47.7 | 1.912–1.907 | 8–10 |
| 48.2–48.3 | 1.888–1.884 | 3–6 |
| 48.85–49.0 | 1.864–1.859 | 0–7 |
| 49.05–49.5 | 1.857–1.841 | 5–7 |
| 50.01–50.05 | 1.824–1.822 | 0–5 |
| 52.3–52.4 | 1.749–1.746 | 0–3 |
| 52.9–53.0 | 1.731–1.728 | 11–16 |
| 53.6 | 1.710 | 0–2 |
| 54.6–54.7 | 1.681–1.678 | 8–16 |
| 55.1–55.2 | 1.667–1.664 | 0–3 |

Preparation 15

(a) SAPO-42, which appears to be structurally similar to the aluminosilicate zeolite A, is found to be produced by the extended aging at lower temperatures of a gel composition which otherwise yields SAPO-20, a silicoaluminophosphate which has structural similarity to the aluminosilicate sodalite. The gel involved was prepared from two mixtures. A first mixture was formed by combining a solution of 76.9 grams of 85 wt. % orthophosphoric acid (H₃PO₄) in 60.1 grams of water with 45.8 grams of a hydrated aluminum oxide (a pseudo-boehmite phase, 74.2 wt. % Al₂O₃, 25.8 wt. % H₂O) and stirring until homogeneous. To this mixture was added a solution of 192.3 grams of tetramethylammonium hydroxide pentahydrate (TMAOH5H₂O) in 121.1 grams of water and the mixture stirred until homogeneous. A second mixture was prepared by combining a solution of 23.5 grams of sodium aluminate (1.21Na₂O.Al₂O₃.3.2H₂O) in 38.0 grams of water with 80.1 grams of an aqueous solution of 30 wt. % SiO₂ and 8.2 additional grams of water. To this mixture was added 98.7 grams of the first-prepared mixture, and the resulting composition stirred until homogeneous. The resulting gel had a composition in molar oxide ratios of:

1.2Na₂O:1.1(TMA)₂O:4.0SiO₂:1.66Al₂O₃:0.66-P₂O₅:95H₂O

Part of the reaction mixture was placed in a sealed inert plastic container and heated in an oven at 100° C. at autogenous pressure for 480 hours. The solid reaction product was recovered by centrifugation, washed with water, and dried in air at 100° C. The above product had an X-ray powder diffraction pattern characterized by the following data:

TABLE CC

| 2θ | d | 100 × I/I₀ |
|---|---|---|
| 7.4 | 11.9 | 71 |
| 10.4 | 8.51 | 55 |
| 12.7 | 6.97 | 61 |
| 13.9 | 6.37 | 7 |
| 16.35 | 5.42 | 31 |
| 17.9 | 4.96 | 13 |
| 21.6 (sh) | 4.13 | 68 |
| 21.9 | 4.06 | |
| 23.1 | 3.85 | 17 |
| 24.25 | 3.67 | 100 |
| 26.4 | 3.376 | 29 |
| 27.4 | 3.255 | 83 |
| 30.25 | 2.955 | 75 |
| 31.1 | 2.876 | 15 |
| 32.9 | 2.722 | 19 |
| 33.7 | 2.660 | 9 |
| 34.45 | 2.603 | 37 |
| 36.05 | 2.491 | 19 |
| 36.9 | 2.436 | 5 |
| 38.35 | 2.347 | 5 |
| 40.5 | 2.227 | 7 |
| 41.85 | 2.158 | 11 |
| 42.55 | 2.125 | 6 |
| 43.15 | 2.096 | 3 |
| 43.85 | 2.065 | 1 |
| 44.5 | 2.036 | 9 |
| 47.7 | 1.907 | 8 |
| 48.3 | 1.884 | 4 |
| 49.0 | 1.859 | 1 |
| 49.5 | 1.841 | 6 |
| 50.05 | 1.822 | 4 |
| 52.4 | 2.746 | 3 |
| 53.0 | 1.728 | 16 |
| 53.6 | 1.710 | 2 |
| 54.65 | 1.679 | 16 |
| 55.2 | 1.664 | 2 |

By chemical analysis, the composition of the crystalline product was found to be 11.3 wt.-% Na₂O, 38.3 wt.-% SiO₂, 25.6 wt.-% Al₂O₃, 1.6 wt.-% C, 4.4 wt.-% P₂O₅, 19.9 wt.-% LOI, giving a product composition in molar oxide ratios of:

0.07(TMA)₂O:2.5SiO₂:0.7Na₂O:Al₂O₃:0.1P₂O₅:3.7-H₂O which corresponds in turn to the essential formula (anhydrous basis):

0.03(TMA):(Si₀.₅₃Al₀.₄₂P₀.₀₄)O₂

(b) A portion of the SAPO-42 part (a) supra was calcined in air at 550° C. for 2 hours. Adsorption capacities were measured on this calcined sample using a standard McBain-Bakr gravimetric adsorption apparatus. The following data were obtained on a sample activated at 350° C.

| | Kinetic Diameter, Å | Pressure, Torr | Temp., °C. | Wt. % Adsorbed |
|---|---|---|---|---|
| O₂ | 3.46 | 98.5 | −183 | 12.6 |
| O₂ | 3.46 | 740. | −183 | 17.0 |
| n-Hexane | 4.3 | 53.5 | 24 | 7.4 |
| Isobutane | 5.0 | 751. | 24 | 1.0 |
| H₂O | 2.65 | 4.6 | 23 | 15.5 |
| H₂O | 2.65 | 19.4 | 24 | 21.0 |

The pore size of the calcined product is >4.3 Å, as shown by the adsorption of n-hexane.

SAPO-44

The species SAPO-44 as referred to herein is a silicoaluminophosphate material having a three-dimensional microporous crystal framework structure of $PO_2^+$, $AlO_2^-$ and $SiO_2$ tetrahedral units, and whose essential empirical chemical composition on an anhydrous basis is:

$$mR: (Si_xAl_yP_x)O_2$$

wherein "R" represents at least one organic templating agent present in the intracrystalline pore system; "m" represents the moles of "R" present per mole of $(Si_xAl_yP_z)O_2$ and has a value of from zero to 0.3, "x", "y" and "z" represent respectively, the mole fractions of silicon, aluminum and phosphorus present in the oxide moiety, said mole fractions being within the compositional area bounded by points A, B, C, D and E on the ternary diagram which is FIG. 1, or preferably within the area bounded by points a, b, c, d and e on the ternary diagram which is FIG. 2, said silicoaluminophosphate having a characteristic X-ray powder diffraction pattern which contains at least the d-spacings set forth below in Table XXI. In the form as synthesized in accordance with the process of this invention, "m" has a value of from 0.03 to 0.3.

TABLE XXI

| $2\theta$ | d | Relative Intensity |
|---|---|---|
| 9.4–9.55 | 9.41–9.26 | VS |
| 13.0–13.1 | 6.81–6.76 | W–M |
| 16.1–16.2 | 5.50–5.47 | W–M |
| 20.75–20.85 | 4.28–4.26 | S–VS |
| 30.85–30.95 | 2.898–2.889 | M–S |

All of the as-synthesized SAPO-44 compositions for which X-ray powder diffraction data have presently been obtained have patterns which are within the generalized pattern of Table XXII, below:

TABLE XXII

| $2\theta$ | d | $100 \times I/I_o$ |
|---|---|---|
| 9.4–9.5 | 9.41–9.26 | 97–100 |
| 10.95 | 8.08 | 4–12 |
| 13.0–13.1 | 6.81–6.76 | 15–31 |
| 13.3–13.4 | 6.66–6.61 | 1–6 |
| 13.75–13.8 | 6.44–6.42 | 3 |
| 16.1–16.2 | 5.50–5.47 | 31–55 |
| 17.35–17.4 | 5.11–5.10 | 9–16 |
| 19.0 | 4.67 | 6 |
| 20.75–20.85 | 4.28–4.26 | 68–100 |
| 21.0–21.1 (sh) | 4.23–4.21 | |
| 21.8–21.9 | 4.08–4.06 | 25 |
| 22.6–22.7 | 3.93–3.92 | 3–7 |
| 23.1 | 3.85 | 7–12 |
| 24.45–24.55 | 3.641–3.626 | 55–74 |
| 26.15–26.2 | 3.408–3.401 | 16–22 |
| 26.9 | 3.314 | 1–2 |
| 27.8–27.9 | 3.209–3.198 | 7–10 |
| 28.5 | 3.132 | 2–7 |
| 29.7 | 3.008 | 3–4 |
| 30.2 | 2.959 | 18–20 |
| 30.85–30.95 | 2.898–2.889 | 45–50 |
| 31.6–31.65 | 2.831–2.827 | 1 |
| 32.15–32.2 | 2.784–2.780 | 2–7 |
| 32.55–32.6 | 2.751–2.747 | 1–3 |
| 33.0 | 2.714 | 5 |
| 34.8 | 2.578 | 1–3 |
| 35.6 | 2.522 | 8–11 |
| 38.5–38.6 | 2.338–2.332 | 1 |
| 39.2 | 2.298 | 1 |
| 39.9–40.0 | 2.259–2.254 | 1–2 |
| 42.2–42.3 | 2.141–2.137 | |
| 42.6 (sh) | 2.122 | 4 |
| 42.9 (sh) | 2.108 | 4 |
| 46.3–43.7 | 2.076–2.071 | 2–3 |
| 44.3–44.4 | 2.045–2.040 | 1 |
| 45.1–45.2 | 2.010–2.006 | 1 |
| 46.1–46.2 | 1.969–1.965 | 1 |
| 47.2–47.3 | 1.926–1.922 | 2 |
| 48.15–48.2 | 1.890–1.888 | 6–7 |
| 48.7–48.8 | 1.870–1.866 | 5 |
| 50.4–50.5 | 1.811–1.807 | 7–9 |
| 51.2–51.3 | 1.784–1.781 | 1 |
| 52.1–52.2 | 1.755–1.752 | 2 |
| 53.9–54.0 | 1.701–1.698 | 6–8 |

Preparation 16

A SAPO species which has no known structural counterpart in the $AlPO_4$ or zeolite series, SAPO-44, is prepared by combining 23.1 grams of 85 wt.-% orthophosphoric acid ($H_3PO_4$) and 57.8 grams of water with 40.9 grams of aluminum isopropoxide ($Al(OC_3H_7)_3$) and 5.0 grams of water and the mixture stirred until homogeneous. To this mixture were added 12.0 grams of an aqueous sol of 30 wt.-% $SiO_2$ and 5.0 grams of water and the mixture stirred until homogeneous. To this mixture were added 9.9 grams of cyclohexylamine ($C_6H_{11}NH_2$) and 5.0 grams of water, and the mixture stirred until homogeneous. The composition of the final reaction mixture in molar oxide ratios was:

$$C_6H_{11}NH_2:0.6SiO_2:Al_2O_3:P_2O_5:50H_2O$$

Part of the reaction mixture was placed in a stainless steel pressure vessel lined with an inert plastic material and heated in an oven at 200° C. at autogenous pressure for 52 hours. The solid reaction product was recovered by centrifugation, washed with water, and dried in air at 100° C. The above product was impure but the major phase (SAPO-44) had an X-ray powder diffraction pattern characterized by the following data:

TABLE DD

| $2\theta$ | d | $100 \times I/I_o$ |
|---|---|---|
| 7.5* | 11.8 | 2 |
| 9.5 | 9.31 | 100 |
| 10.95 | 8.08 | 4 |
| 13.0 | 6.81 | 31 |
| 13.3 | 6.66 | 1 |
| 13.75 | 6.44 | 3 |
| 14.9* | 5.95 | 1 |
| 16.15 | 5.49 | 51 |
| 17.4 | 5.10 | 9 |
| 19.0 | 4.67 | 6 |
| 19.7* | 4.51 | 1 |
| 20.85 | 4.26 | |
| 21.1 (sh)* | 4.21 | 98 |
| 21.9 | 4.06 | 25 |
| 22.5 (sh)* | 3.95 | |
| 22.7 | 3.92 | 7 |
| 23.1 | 3.85 | 12 |
| 24.55 | 3.626 | 55 |
| 25.9 (sh)* | 3.440 | |
| 26.2 | 3.401 | 22 |
| 26.9 | 3.314 | 1 |
| 27.9 | 3.198 | 10 |
| 28.5 | 3.132 | 2 |
| 29.0* | 3.079 | 1 |
| 29.7 | 3.008 | 4 |
| 30.2* | 2.959 | 18 |

TABLE DD-continued

| 2θ | d | 100 × I/I₀ |
|---|---|---|
| 30.9 | 2.894 | 80 |
| 31.6 | 2.831 | 1 |
| 32.15 | 2.784 | 2 |
| 32.55 | 2.751 | 3 |
| 33.0 | 2.714 | 5 |
| 33.6* | 2.667 | 1 |
| 34.8* | 2.578 | 3 |
| 35.6 | 2.522 | 11 |
| 38.5 | 2.338 | 1 |
| 39.2 | 2.298 | 1 |
| 39.9 | 2.259 | 2 |
| 42.3 | 2.137 | } 4 |
| 42.6 (sh) | 2.122 | |
| 43.7 | 2.071 | 3 |
| 44.4 | 2.040 | 1 |
| 45.2 | 2.006 | 1 |
| 46.2 | 1.965 | 1 |
| 47.3 | 1.922 | 2 |
| 48.2* | 1.888 | 6 |
| 48.8 | 1.866 | 5 |
| 50.5 | 1.807 | 9 |
| 51.2 | 1.784 | 1 |
| 52.2 | 1.752 | 2 |
| 54.0 | 1.698 | 8 |

*Possibly contains peak of another phase

Chemical analysis indicated the composition of the product SAPO-44 to be

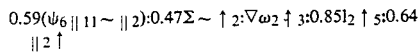

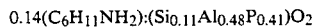

This corresponds to an essential empirical formula (anhydrous basis) of $0.14(C_6H_{11}NH_2):(Si_{0.11}Al_{0.48}P_{0.41})O_2$ (b) A portion of the solid crystalline product obtained by heating a portion of the above reaction mixture at 200° C. for 168 hours and exhibiting an X-ray powder diffraction pattern essentially identical to that above was calcined in air at about 550° C. for 2 hours. The calcined product had an X-ray powder diffraction pattern characterized by the following data:

TABLE EE

| 2θ | d | 100 × I/I₀ |
|---|---|---|
| 7.4* | 11.9 | 1 |
| 9.5 | 9.3 | 100 |
| 10.9 | 8.12 | 3 |
| 12.95 | 6.84 | 46 |
| 13.4 | 6.61 | 3 |
| 13.9 | 6.37 | 3 |
| 16.1 | 5.50 | 22 |
| 17.8 | 4.98 | 22 |
| 19.1 | 4.65 | 3 |
| 20.75 | 4.28 | 54 |
| 22.1 | 4.02 | 5 |
| 22.65 | 3.925 | 1 |
| 23.2 | 3.834 | 11 |
| 24.9 | 3.576 | 23 |
| 26.1 | 3.414 | 18 |
| 27.2 | 3.278 | 1 |
| 27.8 | 3.209 | 3 |
| 28.2 | 3.164 | 7 |
| 29.2 | 3.058 | 1 |
| 29.75 | 3.003 | 3 |
| 30.8 | 2.903 | 40 |
| 31.2 | 2.867 | 16 |
| 31.8 | 2.814 | 1 |
| 32.5 | 2.755 | 2 |
| 33.6* | 2.667 | 3 |
| 34.8* | 2.578 | 5 |
| 35.2 | 2.550 | 1 |
| 36.2 | 2.481 | 3 |
| 43.0 | 2.103 | 1 |
| 48.2* | 1.888 | 1 |
| 49.2 | 1.852 | 2 |
| 51.1 | 1.787 | 2 |
| 53.8 | 1.704 | 1 |
| 54.6 | 1.681 | 1 |

*possibly contains peak from another phase (c) Adsorption capacities were measured on this calcined product using a standard McBain-Bakr gravimetric adsorption apparatus. The following data were obtained on a sample activated at 350° C.:

| | Kinetic Diameter, Å | Pressure, Torr | Temp., °C. | Wt % Adsorbed |
|---|---|---|---|---|
| O₂ | 3.46 | 98 | −183 | 25.5 |
| O₂ | 3.46 | 746 | −183 | 32.3 |
| n-hexane | 4.3 | 48 | 23.9 | 3.6 |
| isobutane | 5.0 | 101 | 25.4 | 0 |

The pore size of the calcined product is 4.3 Å and 5.0 Å, as shown by adsorption of n-hexane, kinetic diameter of 4.3 Å and nil adsorption of isobutane, kinetic diameter of 5.0 Å.

SAPO-31

The species SAPO-31 as referred to herein is a silicoaluminophosphate having a three-dimensional microporous crystal framework structure of $PO_2^+$, $AlO_2^-$ and $SiO_2$ tetrahedral units, and whose essential empirical chemical composition on an anhydrous basis is:

wherein R represents at least one organic templating agent present in the intracrystalline pore system; "m" represents the moles of "R" present per mole of $(Si_xAl_yP_z)O_2$ and has a value of from zero to 0.3; "x", "y" and "z" represent respectively, the mole fractions of silicon, aluminum and phosphorus present in the oxide moiety, said mole fractions being within the compositional area bounded by points A, B, C, D and E on the ternary diagram which is FIG. 1, or preferably within the area bounded by points a, b, c, d and e on the ternary diagram which is FIG. 2, said silicoaluminophosphate having a characteristic X-ray powder diffraction pattern which contains at least the d-spacings set forth below in Table XXIII. In the form as synthesized in accordance with the process of this invention, "m" has a value of from 0.02 to 0.3.

TABLE XXIII

| 2θ | d | Relative Intensity |
|---|---|---|
| 8.5–8.6 | 10.40–10.28 | M–S |
| 20.2–20.3 | 4.40–4.37 | M |
| 21.9–22.1 | 4.06–4.02 | W–M |
| 22.6–22.7 | 3.93–3.92 | VS |
| 31.7–31.8 | 2.823–2.814 | W–M |

All of the as-synthesized SAPO-31 compositions for which X-ray powder diffraction data have presently been obtained have patterns which are within the generalized pattern of Table XXIV, below.

TABLE XXIV

| 2θ | d | 100 × I/I_o |
|---|---|---|
| 6.1 | 14.5 | 0-1 |
| 8.5-8.6* | 10.40-10.28 | 60-72 |
| 9.5 | 9.31 | 7-14 |
| 13.2-13.3* | 6.71-6.66 | 1-4 |
| 14.7-14.8 | 6.03-5.99 | 1-2 |
| 15.7-15.8* | 5.64-5.61 | 1-8 |
| 17.05-17.1 | 5.20-5.19 | 2-4 |
| 18.3-18.4 | 4.85-4.82 | 2-3 |
| 20.2-20.3 | 4.40-4.37 | 44-55 |
| 21.1-21.2* | 4.21-4.19 | 6-28 |
| 21.9-22.1* | 4.06-4.02 | 32-38 |
| 22.6-22.7* | 3.93-3.92 | 100 |
| 23.3-23.35* | 3.818-3.810 | 2-20 |
| 25.1* | 3.548 | 3-4 |
| 25.65-25.75 | 3.473-3.460 | 2-3 |
| 26.5* | 3.363 | 1-4 |
| 27.9-28.0 | 3.198-3.187 | 8-10 |
| 28.7* | 3.110 | 0-2 |
| 29.7 | 3.008 | 4-5 |
| 31.7-31.8 | 2.823-2.814 | 15-18 |
| 32.9-33.0* | 2.722-2.714 | 0-3 |
| 35.1-35.2 | 2.557-2.550 | 5-8 |
| 36.0-36.1 | 2.495-2.488 | 1-2 |
| 37.2 | 2.417 | 1-2 |
| 37.9-38.1* | 2.374-2.362 | 2-4 |
| 39.3 | 2.292 | 2-3 |
| 43.0-43.1* | 2.103-2.100 | 1 |
| 44.8-45.2* | 2.023-2.006 | 1 |
| 46.6 | 1.949 | 1-2 |
| 47.4-47.5 | 1.918 | 1 |
| 48.6-48.7 | 1.873-1.870 | 2 |
| 50.7-50.8 | 1.801-1.797 | 1 |
| 51.6-51.7 | 1.771-1.768 | 2-3 |
| 55.4-55.5 | 1.658-1.656 | 1 |

*Possibly contains peak from minor impurity

Preparation 17

SAPO-31 was crystallized from a reaction mixture prepared by combining 81.7 grams of aluminum isopropoxide (Al(OC$_3$H$_7$)$_3$) with 46.1 grams of 85 wt. % orthophosphoric acid (H$_3$PO$_4$) and 85.0 grams of water and stirring until homogeneous. To this mixture were added 24.0 grams of an aqueous sol of 30 wt. % SiO$_2$ and 42.8 grams of water, and the mixture stirred until homogeneous. To this mixture were added 20.2 grams of di-n-propylamine (Pr$_2$NH) and 34.0 grams of water, and the mixture stirred until homogeneous. To this mixture was added 5.8 grams of AlPO$_4$-31 seed crystals and the mixture stirred until homogeneous. The composition of the final reaction mixture in molar oxide ratios was:

Pr$_2$NH:0.6SiO:Al$_2$O$_3$:P$_2$O$_5$:50H$_2$O and contained 10 wt. % AlPO$_4$-31 seed crystals based on the solids content. A portion of this reaction mixture was placed in a stainless steel pressure vessel lined with an inert plastic material and heated in an oven at 200° C. at autogenous pressure for 24 hours. The solid reaction product was recovered by filtration, washed with water, and dried in air at 100° C. The chemical composition of the SAPO-31 product in terms of molar oxide ratios (anhydrous basis) was:

0.16(Pr$_2$NH):Al$_2$O$_3$:0.15SiO$_2$:0.83P$_2$O$_5$ which corresponds to the formula:

0.04Pr$_2$NH:(Si$_{0.04}$Al$_{0.53}$P$_{0.43}$)O$_2$

The X-ray powder diffraction pattern of the SAPO-31-containing product was characterized by the following data:

TABLE EF

| 2θ | d | 100 × I/I_o |
|---|---|---|
| 7.25* | 12.193 | (sh) |
| 8.539 | 10.355 | 72 |
| 9.530* | 9.280 | 14 |
| 13.279* | 6.778 | 4 |
| 15.774* | 5.618 | 8 |
| 17.104 | 5.184 | 6 |
| 18.380 | 4.827 | 3 |
| 20.280 | 4.379 | 43 |
| 20.5* | 4.332 | (sh) |
| 21.153* | 4.200 | 22 |
| 22.033 | 4.034 | 28 |
| 22.662* | 3.924 | 100 |
| 23.316 | 3.815 | 14 |
| 25.145 | 3.542 | 3 |
| 25.718 | 3.464 | 3 |
| 26.566* | 3.355 | 3 |
| 26.701 | 3.339 | 4 |
| 27.976 | 3.189 | 9 |
| 28.810* | 3.099 | 4 |
| 29.797 | 2.998 | 6 |
| 31.760 | 2.817 | 16 |
| 33.016 | 2.713 | 3 |
| 34.367* | 2.609 | 2 |
| 35.215 | 2.549 | 8 |
| 36.090 | 2.489 | 2 |
| 37.777* | 2.381 | 3 |
| 37.938* | 2.372 | 3 |
| 38.113 | 2.361 | 3 |
| 39.402 | 2.287 | 3 |
| 39.641 | 2.274 | 2 |
| 40.195 | 2.244 | 2 |
| 44.891* | 2.019 | 2 |
| 45.345 | 2.000 | 2 |
| 46.708 | 1.945 | 2 |
| 51.670 | 1.769 | 3 |

*contains impurity peak

The X-ray powder diffraction pattern of the SAPO-31-containing product after calcination in air for 7 hours at 550° C. was characterized by the following data:

TABLE FF

| 2θ | d | 100 × I/I_o |
|---|---|---|
| 7.7 | 11.5 | (sh) |
| 8.5 | 10.4 | 100 |
| 8.9 | 9.94 | (sh) |
| 9.6 | 9.21 | (sh) |
| 9.8 | 9.03 | 3 |
| 12.85 | 6.89 | 1 |
| 14.7 | 6.03 | 7 |
| 16.1 | 5.50 | 3 |
| 17.05 | 5.20 | 10 |
| 18.45 | 4.81 | 2 |
| 20.3 | 4.37 | 34 |
| 21.4 | 4.15 | (sh) |
| 22.05 | 4.03 | 37 |
| 22.6 | 3.93 | 81 |
| 23.35 | 3.81 | 3 |
| 25.1 | 3.548 | 3 |
| 25.7 | 3.466 | 4 |
| 27.9 | 3.198 | 11 |
| 29.7 | 3.008 | 8 |
| 31.0 | 2.885 | 1 |
| 31.7 | 2.823 | 18 |
| 32.4 | 2.763 | 1 |
| 35.1 | 2.557 | 7 |
| 36.2 | 2.481 | 2 |
| 37.2 | 2.417 | 2 |
| 37.6 | 2.392 | 2 |
| 38.3 | 2.350 | 2 |
| 39.3 | 2.292 | 3 |
| 39.6 | 2.276 | 1 |
| 40.3 | 2.238 | 3 |
| 43.2 | 2.094 | 1 |
| 44.0 | 2.058 | 1 |

TABLE FF-continued

| $2\theta$ | d | $100 \times I/I_o$ |
|---|---|---|
| 45.0 | 2.014 | 2 |
| 47.1 | 1.929 | 3 |
| 47.6 | 1.910 | 2 |
| 48.6 | 1.873 | 2 |
| 49.2 | 1.852 | 1 |
| 50.8 | 1.797 | 1 |
| 51.6 | 1.771 | 4 |
| 55.6 | 1.653 | 1 |

(b) Adsorption capacities were measured on the product of part (a). The following data were obtained on a sample activated at 350° C. in vacuum.

| | Kinetic Diameter, A | Pressure Torr | Temp., °C. | Wt. % Adsorbed |
|---|---|---|---|---|
| $O_2$ | 3.46 | 99 | −183 | 8.8 |
| $O_2$ | 3.46 | 740 | −183 | 15.4 |
| $H_2O$ | 2.65 | 4.6 | 23 | 6.9 |
| $H_2O$ | 2.65 | 19.4 | 24 | 21.1 |
| Cyclohexane | 6.0 | 49 | 25 | 7.2 |
| Neopentane | 6.2 | 400 | 24 | 5.9 |

It is apparent from these data that the pore size of SAPO-31 is greater than 6.2 A.

SAPO-41

The species SAPO-41 as referred to herein is a silicoaluminophosphate having a three-dimensional microporous crystal framework structure of $PO_2^+$, $AlO_2^-$ and $SiO_2$ tetrahedral units, and whose essential empirical chemical composition on an anhydrous basis is:

mR: $(Si_xAl_yP_z)O_2$ wherein R represents at least one organic templating agent present in the intracrystalline pore system; "m" represents the moles of "R" present per mole of $(Si_xAl_yP_z)O_2$ and has a value of from zero to 0.3; "x", "y" and "z" represent respectively, the mole fractions of silicon, aluminum and phosphorus present in the oxide moiety, said mole fractions being within the compositional area bounded by points A, B, C, D and E on the ternary diagram which is FIG. 1, or preferably within the area bounded by points a, b, c, d and e on the ternary diagram which is FIG. 2, said silicoaluminophosphate having a characteristic X-ray powder diffraction pattern which contains at least the d-spacings set forth below in Table XXV. In the form as synthesized in accordance with the process of this invention, "m" has a value of from 0.02 to 0.3.

TABLE XXV

| $2\theta$ | d | Relative Intensity |
|---|---|---|
| 13.6-13.8 | 6.51-6.42 | W-M |
| 20.5-20.6 | 4.33-4.31 | W-M |
| 21.1-21.3 | 4.21-4.17 | VS |
| 22.1-22.3 | 4.02-3.99 | M-S |
| 22.8-23.0 | 3.90-3.86 | M |
| 23.1-23.4 | 3.82-3.80 | W-M |
| 25.5-25.9 | 3.493-3.44 | W-M |

All of the as-synthesized SAPO-41 compositions for which X-ray powder diffraction data have presently been obtained have patterns which are within the generalized pattern of Table XXVI, below.

TABLE XXVI

| $2\theta$ | d | $100 \times I/I_o$ |
|---|---|---|
| 6.7-6.8 | 13.19-12.99 | 15-24 |
| 9.6-9.7 | 9.21-9.11 | 12-25 |
| 13.6-13.8 | 6.51-6.42 | 10-28 |
| 18.2-18.3 | 4.87-4.85 | 8-10 |
| 20.5-20.6 | 4.33-4.31 | 10-32 |
| 21.1-21.3 | 4.21-4.17 | 100 |
| 22.1-22.3 | 4.02-3.99 | 45-82 |
| 22.8-23.0 | 3.90-3.87 | 43-58 |
| 23.1-23.4 | 3.82-3.80 | 20-30 |
| 25.2-25.5 | 3.53-3.49 | 8-20 |
| 25.5-25.9 | 3.493-3.44 | 12-28 |
| 29.3-29.5 | 3.048-3.028 | 17-23 |
| 31.4-31.6 | 2.849-2.831 | 5-10 |
| 33.1-33.3 | 2.706-2.690 | 5-7 |
| 37.6-37.9 | 2.392-2.374 | 10-15 |
| 38.1-38.3 | 2.362-2.350 | 7-10 |
| 39.6-39.8 | 2.276-2.265 | 2-5 |
| 42.8-43.0 | 2.113-2.103 | 5-8 |
| 49.0-49.3 | 1.859-1.848 | 1-8 |
| 51.5 | 1.774 | 0-8 |

Preparation 18

(a) A reaction mixture was prepared by combining 9.22 grams of 85 wt. % orthophosphoric acid ($H_3PO_4$) and 5.78 grams of water, to which was added 5.52 grams of hydrated aluminum oxide, (a pseudo-boehmite phase, 74.2 wt. % $Al_2O_3$, 25.8 wt. % $H_2O$) and stirred until homogeneous. To this mixture was added a mixture of 1.04 grams of a fumed silica (92.8 wt. % $SiO_2$, 7.2 wt. % $H_2O$) in 41.67 grams of an aqueous solution of 25.9 wt. % tetra-n-butylammonium hydroxide (TBAOH). This mixture was stirred until homogeneous and then another 41.67 grams of TBAOH was slowly added with stirring until a homogeneous mixture was obtained. The composition of the final reaction mixture in molar oxide ratios was:

$(TBA)_2O:Al_2O_3:P_2O_5:0.4SiO_2:98.7H_2O$

A portion of the reaction mixture was sealed in a stainless steel pressure vessel lined with an inert plastic material and heated in an oven at 200° C. at autogenous pressure for 144 hours. The solid reaction product was recovered by centrifuging and washing with water, and dried in air at room temperature. The product had an X-ray powder diffraction pattern characterized by the following data:

TABLE HH

| $2\theta$ | d | $100 \times I/I_o$ |
|---|---|---|
| 6.7 | 13.19 | 24 |
| 9.6 | 9.21 | 25 |
| 13.6 | 6.51 | 28 |
| 18.2 | 4.87 | 10 |
| 20.5 | 4.33 | 10 |
| 21.1 | 4.21 | 100 |
| 22.1 | 4.02 | 82 |
| 22.8 | 3.90 | 43 |
| 23.1 | 3.85 | 30 |
| 25.3 | 3.52 | 20 |
| 25.7 | 3.47 | 28 |
| 29.3 | 3.048 | 23 |
| 31.4 | 2.848 | 10 |
| 33.1 | 2.706 | 7 |
| 37.6 | 2.392 | 15 |
| 38.1 | 2.362 | 7 |
| 39.6 | 2.276 | 5 |
| 43.0 | 2.103 | 8 |
| 49.1 | 1.855 | 8 |
| 51.5 | 1.774 | 8 |

By chemical analysis the composition of the SAPO-41 was found to be 5.2 wt. % C; 38.1 wt. % Al$_2$O$_3$; 41.1 wt. % P$_2$O$_5$; 7.1 wt. % SiO$_2$; and by difference, LOI was 13.7 wt. %; giving a product composition in terms of molar oxide ratios of:

0.036(TBA)$_2$O:1.0Al$_2$O$_3$:0.77P$_2$O$_5$:0.32 SiO$_2$:1.0H$_2$O which corresponds to the formula 0.02TBA:(Si$_{0.08}$Al$_{0.52}$P$_{0.40}$)O$_2$ (b) A portion of the above solid product was calcined in air at 600° C. for 2 hours and then at 700° C. for 1 hour. The calcined product had an X-ray powder diffraction pattern characterized by the following data:

TABLE JJ

| 2θ | d | 100 × I/I$_o$ |
|---|---|---|
| 6.7 | 13.19 | 17 |
| 9.7 | 9.12 | 33 |
| 13.6 | 6.51 | 27 |
| 18.4 | 4.82 | 10 |
| 20.5 | 4.33 | 6 |
| 21.3 | 4.17 | 100 |
| 22.3 | 3.99 | 62 |
| 22.8 | 3.90 | 38 |
| 23.0 | 3.87 | 36 |
| 25.4 | 3.52 | 25 |
| 25.7 | 3.466 | 23 |
| 28.1 | 3.175 | 4 |
| 29.4 | 3.038 | 19 |
| 31.4 | 2.849 | 10 |
| 33.2 | 2.698 | 10 |
| 36.7 | 2.449 | 4 |
| 37.9 | 2.374 | 10 |
| 38.4 | 2.344 | 4 |
| 39.7 | 2.270 | 4 |
| 43.3 | 2.089 | 6 |
| 51.5 | 1.774 | 2 |

(c) Adsorption capacities were measured on this calcined product of part (b) using a standard McBain-Bakr gravimetric adsorption apparatus. The following data were obtained on a sample activated at 350° C.

| | Kinetic Diameter, A | Pressure Torr | Temp., °C. | Wt. % Adsorbed |
|---|---|---|---|---|
| O$_2$ | 3.46 | 100 | −183 | 9.3 |
| O$_2$ | 3.46 | 750 | −183 | 11.8 |
| Cyclohexane | 6.0 | 60 | 24 | 4.2 |
| Neopentane | 6.2 | 743 | 24 | 1.2 |
| H$_2$O | 2.65 | 4.6 | 24 | 10.4 |
| H$_2$O | 2.65 | 20.0 | 24 | 21.9 |

The pore size of the calcined product is between 6.0 and 6.2 A as shown by adsorption of cyclohexane, kinetic diameter of 6.0 A and negligible adsorption of neopentane, kinetic diameter of 6.2 A.

EDAX (energy dispersive analysis by X-ray) microprobe analysis, performed in conjunction with SEM (scanning electron microscope) study on crystals having a crystal morphology characteristic of SAPO-41 gives the following analysis based on relative peak heights:

| | Rod | Agglomerate |
|---|---|---|
| Si | 0.09 | 0.11 |
| Al | 1.0 | 1.0 |
| P | 0.87 | 0.74 |

EXPERIMENTAL PROCEDURE (LIGHT OLEFIN PRODUCTION)

The production of light olefins in the examples was carried out by mixing about 0.5 gram of a selected SAPO with 2.5 grams of quartz chips (20–30 U.S. Standard mesh). The resulting mixture was then placed in a ¼ inch (outside diameter) No. 304 stainless steel tubular reactor having a wall thickness of 0.035 inch. The tubular reactor was immersed in a fluidized heated sand bath having electrical resistance heaters provided for maintaining the sand bath and the tubular reactor at the desired temperature. Thermocouples were provided for measurement of the reactor temperature.

A selected feedstock was introduced to the tubular reactor by means of a Model 100 Altex Metering Pump (from Altex Corporation, a subsidiary of the Beckmann Corporation) concurrently with a stream of diluent with nitrogen and water (steam) being employed as diluents (unless otherwise noted in the examples hereinafter). The pressure employed in the examples was the autogenous pressure (about one (1) to about two (2) atmospheres unless otherwise noted. The ratios of these components are reported as weight ratios. When nitrogen was employed as a diluent it was introduced at a flow rate of about 5 cubic centimeters per minute.

The effluent from the tubular reactor (the reaction products) was analyzed. The liquid component of the effluent was collected at room temperature and subsequently analyzed by vapor phase chromatography, whereas the gaseous component of the effluent was sampled and analyzed directly from the effluent stream by vapor phase chromatography.

The analyses of both the liquid and vapor components of the effluent from the tubular reactor were carried out by programmed temperature chromatography having a thermal conductivity detector with a programmed increase in the chromatographic column's temperature over the chromatographic analysis. The analysis of the liquid and vaporous components of the effluent, including the analysis of all standards was carried out using chromatographic techniques by use of the following chromatographic instruments:

| | Phase Analyzed | |
|---|---|---|
| | Liquid | Vapor |
| Chromatograph Column | Varian 3700 20 feet × ⅛ inch (O.D.) stainless steel | Hewlett Packard 11 feet × ⅛ inch (O.D.) stainless steel |
| Packing | 10% Carbowax Chrom T 60/80 mesh | Porapak R |

Unless otherwise noted, the Molar Conversion to total products, based on methanol ethanol, dimethylether, diethylether or mixtures thereof, was 100% with the Molar Efficiency to a particular product being given as a percentage. When a product was not detected (ND) or if only a trace amount was qualitatively detected such is reported as ND or Trace, respectively. Further, although it has been observed that the methane and carbon dioxide formed in the process at temperatures of about 400° C. and higher are primarily derived from contact of the feedstock with the walls of the reactor these values are included since they do affect the efficiency of the overall process although their formation may be minimized by changes in the reactor design. The silicoaluminophosphate employed in the following example is denominated according to the nomenclature of U.S. Pat. No. 4,440,871 as SAPO-34. The SAPOs were calcined prior to their use in the examples. The following examples are provided to exemplify the invention and are not meant to be limiting in any way.

PRODUCTION OF LIGHT OLEFINS: EXAMPLES

Example 1 (Comparative)

A series of experiments were carried out according to the EXPERIMENTAL PROCEDURE to evaluate the molar ratio of ethylene to propylene obtained in the conversion of methanol to light olefin products achieved by use of selected diluents. The results of these experiments were as follows where the diluent, temperature WHSV ($hr^{-1}$) of methanol, molar ratio of diluent to methanol (Diluent/MeOH) and molar ratio of ethylene to propylene (E/P) were as given below in Table I.

TABLE I

| Experiment[1] | Diluent | WHSV (methanol) ($hr^1$) | Diluent MeOH | E/P Ratio |
|---|---|---|---|---|
| A | $N_2$ | 1.12. | 5.1 | 1.64 |
| B | He | 0.97 | 6.0 | 1.60 |
| C | $CO_2$ | 1.00 | 5.8 | 1.68 |
| D[2] | $H_2O/N_2$ | 0.93 | 5.1 | 1.68 |
| E[2] | $H_2O/N_2$ | 1.04 | 3.0 | 1.65 |
| F | $N_2$ | 1.17 | 1.2 | 1.61 |

[1]The temperature was 425° C. in each experiment.
[2]A minor amount of $N_2$ was added (5 cc/min)

Example 2

SAPO-34 was employed as the catalyst for the conversion of methanol to light olefins wherein the diluent was water (Tables II and IV), benzene (Table V) or toluene (Table III). In each case nitrogen was added at a flow rate of about 5 cc/minute. The data in the Tables III and V show a significant increase in the molar ratio of ethylene to propylene in the hydrocarbon products as a result of the use of an aromatic diluent characterized as having molecules with an average kinetic diameter greater than the average pore size of SAPO-34.

TABLE II[1,2]

| Molar Efficiency, % | | |
|---|---|---|
| Ethylene | 45.55 | 48.04 |
| Ethane | 0.88 | 0.85 |
| Propylene | 34.21 | 33.37 |
| Propane | — | — |
| Butenes | 8.37 | 8.05 |
| $C_5$ | 1.88 | 1.37 |
| $C_6$ | 0.69 | 0.22 |
| Methane | 3.95 | 3.99 |
| Carbon Dioxide | 4.47 | 4.13 |
| Run Time, hr | 5.6 | 7.1 |
| Ethylene/Propylene (molar ratio) | 1.33 | 1.44 |

[1]Temperature: 425° C.
[2]WHSV (Methanol) = 0.91 $hr^{-1}$ $H_2O$/MeOH: (by weight) = 70/30 (by mole) = 4.1

TABLE III[1,2]

| Molar Efficiency, % | | |
|---|---|---|
| Ethylene | 59.46 | 61.58 |
| Ethane | 1.76 | 1.66 |
| Propylene | 27.59 | 26.18 |
| Propane | — | — |
| Butenes | 2.80 | 2.61 |

TABLE III[1,2]-continued

| Molar Efficiency, % | | |
|---|---|---|
| $C_5$ | 0.16 | 0.15 |
| $C_6$ | 0.01 | 0.01 |
| Methane | 6.98 | 6.80 |
| Carbon dioxide | 1.24 | 1.00 |
| Run Time, hr | 5.5 | 7.3 |
| Ethylene/Propylene (molar ratio) | 2.16 | 2.35 |

[1]Temperature: 425° C.
[2]WHSV (Methanol) = 0.80 $hr^{-1}$ Toluene/MeOH: (by weight) = 92/8 (by mole) = 4.0

TABLE IV[1,2]

| Molar Efficiency, % | | |
|---|---|---|
| Ethylene | 39.57 | 41.69 |
| Ethane | 0.43 | 0.40 |
| Propylene | 25.25 | 25.27 |
| Propane | — | — |
| Butenes | 6.69 | 6.50 |
| $C_5$ | 0.82 | 0.77 |
| $C_6$ | trace | trace |
| Methane | 7.39 | 7.05 |
| Carbon Dioxide | 19.76 | 18.26 |
| Run Time, hr | 7.8 | 10.0 |
| Ethylene/Propylene (molar ratio) | 1.57 | 1.65 |

[1]Temperature: 425° C.
[2]WHSV (Methanol) = 0.92 $hr^{-1}$ $H_2O$/MeOH: (by weight) = 70/30 (by mole) = 4.1

TABLE V[1,2]

| Molar Efficiency, % | | |
|---|---|---|
| Ethylene | 48.69 | 52.02 |
| Ethane | 0.71 | 0.58 |
| Propylene | 22.82 | 23.72 |
| Propane | — | — |
| Butenes | 4.07 | 2.45 |
| $C_5$ | 0.37 | 0.55 |
| $C_6$ | trace | trace |
| Methane | 11.93 | 11.60 |
| Carbon Dioxide | 11.44 | 9.08 |
| Run Time, hr | 7.3 | 9.7 |
| Ethylene/Propylene (molar ratio) | 2.13 | 2.19 |

[1]Temperature: 425° C.
[2]WHSV (Methanol) = 0.94 $hr^{-1}$ Benzene/MeOH: (by weight) = 90/10 (by mole) = 3.7

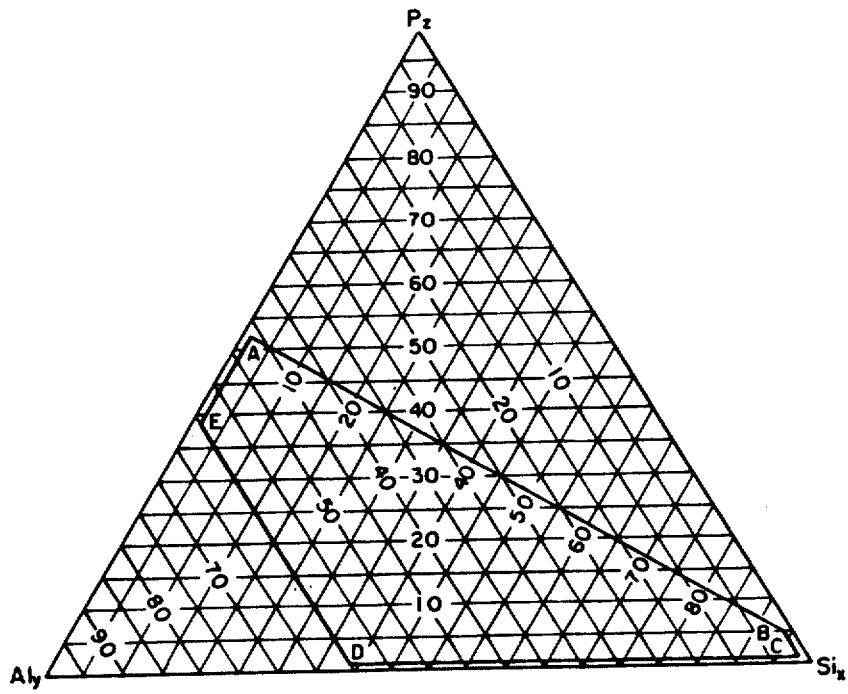

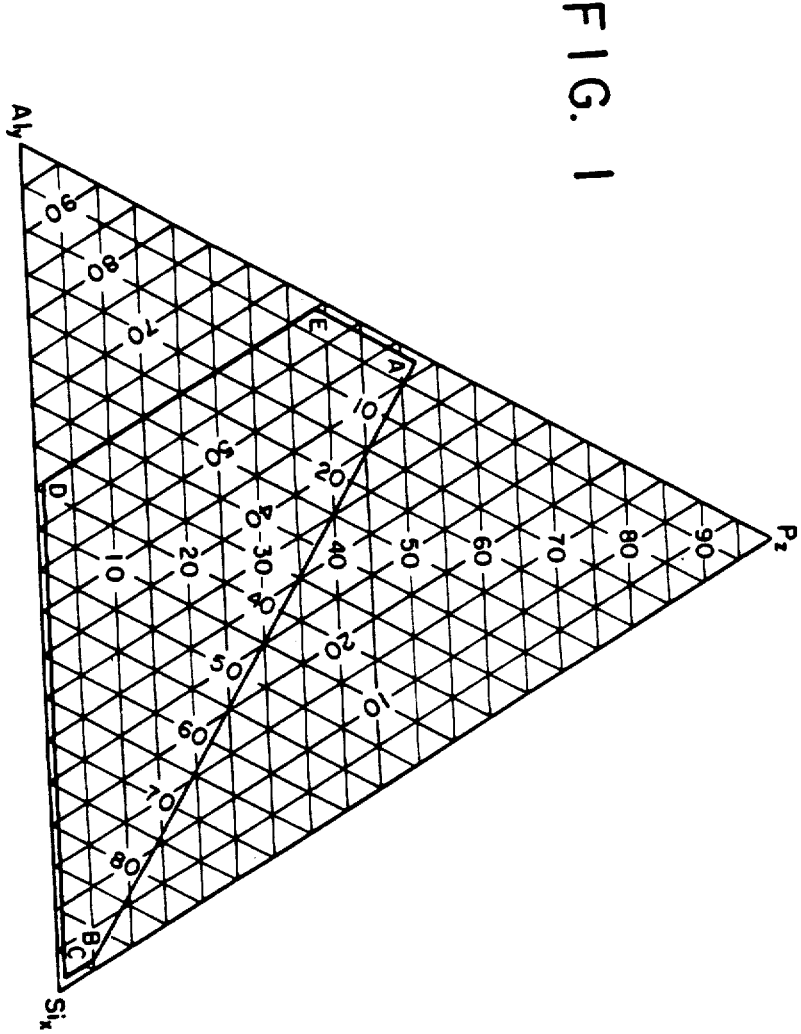

What is claimed is:

1. The process for making light olefins containing 2 to 4 carbon atoms which comprise contacting a feedstock comprising one or more aliphatic hetero compounds with a silicoaluminophosphate molecular sieve in the presence of a diluent wherein the silicoaluminophosphate molecular sieve comprises a microporous crystalline silicoaluminophosphate whose unit empirical formula in the as-synthesized and anhydrous form is $$mR:(Si_xAl_yP_z)O_2$$

wherein "R" represents at least one organic templating agent present in the intracrystalline pore system; "m" has a value of from 0.02 to 0.3; "m" represents the moles of "R" present per mole of $(Si_xAl_yP_z)O_2$; "x", "y" and "z" represent the mole fractions of silicon, aluminum and phosphorus respectively, present as tetrahedral units, said mole fractions being such that they are within the pentagonal compositional area defined by points A, B, C, D and E of the ternary diagram which is FIG. 1, at effective process conditions to produce said light olefins, comprising the improvement of correlating the diluent to the silicoaluminophosphate whereby the average kinetic diameter of the diluent molecules is greater than the average pore size of the silicoaluminophosphate molecular sieve.

2. The process of claim 1 wherein the diluent is an aromatic diluent.

3. The process of claim 1 wherein the silicoaluminophosphate is characterized by adsorption of oxygen and negligible adsorption of isobutane.

4. The process of claim 1 wherein the silicoaluminophosphate is characterized by adsorption of xenon and negligible adsorption of isobutane.

5. The process of claim 1 wherein the silicoaluminophosphate is characterized by adsorption of n-hexane and negligible adsorption of isobutane.

6. The process of claim 1 wherein the silicoaluminophosphate has mole fractions of silicon, aluminum and phosphorus within the pentagonal compositional area defined by points a, b, c, d and e of the ternary diagram which is FIG. 2.

7. The procss of claim 1 wherein the silicoaluminophosphate has the characteristic X-ray powder diffraction pattern which contains at least the d-spacings set forth in Table I.

8. The procss of claim 1 wherein the silicoaluminophosphate has the characteristic X-ray powder diffraction pattern which contains at least the d-spacings set forth in Table III.

9. The process of claim 1 wherein the silicoaluminophosphate has the characteristic X-ray powder diffraction pattern which contains at least the d-spacings set forth in Table V.

10. The process of claim 1 wherein the silicoaluminophosphate has the characteristic X-ray powder diffraction pattern which contains at least the d-spacings set forth in Table VII.

11. The process of claim 1 wherein the silicoaluminophosphate has the characteristic X-ray powder diffraction pattern which contains at least the d-spacings set forth in Table IX.

12. The process of claim 1 wherein the silicoaluminophosphate has the characteristic X-ray powder diffraction pattern which contains at least the d-spacings set forth in Table XI.

13. The process of claim 1 wherein the silicoaluminophosphate has the characteristic X-ray powder diffraction pattern which contains at least the d-spacings set forth in Table XIII.

14. The process of claim 1 wherein the silicoaluminophosphate has the characteristic X-ray powder diffraction pattern which contains at least the d-spacings set forth in Table XV.

15. The process of claim 1 wherein the silicoaluminophosphate has the characteristic X-ray powder diffraction pattern which contains at least the d-spacings set forth in Table XVII.

16. The process of claim 1 wherein the silicoaluminophosphate has the characteristic X-ray powder diffraction pattern which contains at least the d-spacings set forth in Table XIX.

17. The process of claim 1 wherein the silicoaluminophosphate has the characteristic X-ray powder diffraction pattern which contains at least the d-spacings set forth in Table XXI.

18. The process of claim 1 wherein the silicoaluminophosphate has the characteristic X-ray powder diffraction pattern which contains at least the d-spacings set forth in Table XXIII.

19. The process of claim 1 wherein the silicoaluminophosphate has the characteristic X-ray powder diffraction pattern which contains at least the d-spacings set forth in Table XXV.

20. The process of claim 1 wherein said aliphatic hetero compounds are alcohols, ethers, amines, mercaptans, aldehydes, ketones and halides wherein the aliphatic moiety of said aliphatic hetero compounds contains from 1 to about 10 carbon atoms.

21. The process of claim 1 wherein said silicoaluminophosphate molecular sieve has a kinetic pore diameter such that the selectivity to said light olefins is greater than 50 molar percent.

22. The process of claim 1 wherein said diluent is selected from the group consisting of cycloalkanes, pyridine and aromatic compounds of the formula:

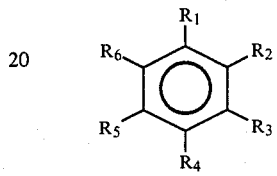

wherein $R_1$, $R_2$, $R_3$, $R_4$, $R_5$, and $R_6$ are alkyl, aralkyl, aryl, alkylaryl or mixtures thereof containing from 1 to 20 carbon or hetero atoms.

23. The process of claim 2 wherein said aromatic diluent is selected from the group consisting of benzene, toluene, o-xylene, m-xylene, p-xylene, hemimellitene, pseudocumene, mesitylene, prehnitene, isodurene, durene, pentamethylbenzene, hexamethylbenzene, ethylbenzene, n-propylbenzene, cumene, n-butylbenzene, isobutylbenzene, sec-butylbenzene, tert-butylbenzene, p-cymene, biphenyl, diphenylmethane, triphenyl, diphenylmethane, triphenyl methane, anthracene; naphthalene; 1,2-diphenylethane and mixtures thereof.

24. The process of claim 1 wherein the feedstock is contacted with said silicoaluminophosphate at a temperature between about 200° and about 700° C.

25. The process of claim 24 wherein the feedstock is contacted with said silicoaluminophosphate at a temperature between about 250° and about 600° C.

26. The process of claim 1 wherein the process is conducted at a pressure between about 0.1 atmosphere and about 1000 atmospheres.

27. The process of claim 26 wherein the process is conducted at a pressure between about 0.1 atmosphere and about 100 atmospheres.

28. The process of claim 1 wherein said process is carried out in the vapor phase.

29. The process of claim 1 wherein said process is carried out in the liquid phase.

30. The process of claim 1 wherein the WHSV is between about 0.01 hr$^{-1}$ and about 100 hr$^{-1}$.

31. The process of claim 1 wherein the WHSV is between about 0.1 hr$^{-1}$ and about 40 hr$^{-1}$.

32. The process of claim 1 wherein the feedstock comprises methanol.

33. The process of claim 1 wherein the feedstock comprises methanol and dimethyl ether.

34. The process of claim 1 wherein the feedstock comprises ethanol.

35. The process of claim 1 wherein the feedstock comprises ethanol and diethyl ether.

36. The process of claim 1 wherein the feedstock consists essentially of methanol, dimethyl ether and said diluent is aromatic selected from the group consisting of benzene, toluene, xylene and mixtures thereof.

37. The process of claim 1 wherein the feedstock comprises at least one of methanol, ethanol and dimethyl ether and said diluent is aromatic selected from the group consisting of benzene, toluene, xylene and mixtures thereof.

38. The process of claim 1 wherein said feedstock comprises of at least one of the methanol, ethanol, and dimethyl ether, said diluent is aromatic and is present in an amount between about 1 and about 99 weight percent based on said feedstock, and said process is carried out at a temperature between about 200° C. and about 700° C., at a pressure between about 0.001 atmospheres and about 1000 atmospheres and at a WHSV between about 0.01 hr$^{-1}$ and about 100 hr$^{-1}$.

* * * * *

UNITED STATES PATENT AND TRADEMARK OFFICE
CERTIFICATE OF CORRECTION

PATENT NO. : 4,677,242

DATED : June 30, 1987

INVENTOR(S) : Steven W. Kaiser

It is certified that error appears in the above-identified patent and that said Letters Patent is hereby corrected as shown below:

The title page should be deleted to appear as per attached title page.

The sheets of drawings consisting of Fig. 1 and Fig. 2 should be added as part of Letters Patent, as shown on the attached sheets.

Signed and Sealed this

Twenty-fifth Day of October, 1988

Attest:

DONALD J. QUIGG

Attesting Officer

Commissioner of Patents and Trademarks

United States Patent [19]

Kaiser

[11] Patent Number: 4,677,242
[45] Date of Patent: * Jun. 30, 1987

[54] PRODUCTION OF LIGHT OLEFINS

[75] Inventor: Steven W. Kaiser, South Charleston, W. Va.

[73] Assignee: Union Carbide Corporation, Danbury, Conn.

[*] Notice: The portion of the term of this patent subsequent to Feb. 12, 2002 has been disclaimed.

[21] Appl. No.: 700,311

[22] Filed: Feb. 11, 1985

Related U.S. Application Data

[63] Continuation-in-part of Ser. No. 426,213, Oct. 4, 1982, Pat. No. 4,499,327.

[51] Int. Cl.⁴ .................................................. C07C 1/00
[52] U.S. Cl. .................................... 585/638; 585/639; 585/640
[58] Field of Search ............... 585/638, 639, 640, 469, 585/733, 357, 603

[56] References Cited

U.S. PATENT DOCUMENTS

| | | | |
|---|---|---|---|
| 4,373,109 | 2/1983 | Olah | 585/638 |
| 4,440,871 | 4/1984 | Lok et al. | 502/214 |
| 4,499,327 | 2/1985 | Kaiser | |
| 4,524,234 | 6/1985 | Kaiser | 585/638 |

FOREIGN PATENT DOCUMENTS 911410 10/1972 Canada
WO82100018 6/1982 PCT Int'l Appl.

Primary Examiner—John Doll
Assistant Examiner—Chung K. Pak
Attorney, Agent, or Firm—Vincent J. Vasta, Jr.

[57] ABSTRACT

The process for the production of light olefins from a feedstock comprising at least an aliphatic hetero compound comprising contacting said feedstock in the presence of an aromatic diluent with a silicoaluminophosphate molecular sieve at effective process conditions to produce light olefins.

38 Claims, 2 Drawing Figures